US012668780B2

(12) United States Patent
Zhang et al.

(10) Patent No.: US 12,668,780 B2
(45) Date of Patent: Jun. 30, 2026

(54) MACROPHAGE-SPECIFIC CHIMERIC ANTIGEN RECEPTOR, CONTROLLABLE POLARIZED MONOCYTE/MACROPHAGE EXPRESSING THE RECEPTOR, AND PREPARATION METHOD AND USE THEREOF

(71) Applicant: ZHEJIANG UNIVERSITY, Hangzhou (CN)

(72) Inventors: Jin Zhang, Hangzhou (CN); Anhua Lei, Hangzhou (CN); Lin Tian, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 640 days.

(21) Appl. No.: 17/761,525

(22) PCT Filed: Sep. 10, 2021

(86) PCT No.: PCT/CN2021/117808
§ 371 (c)(1),
(2) Date: Mar. 17, 2022

(87) PCT Pub. No.: WO2022/262130
PCT Pub. Date: Dec. 22, 2022

(65) Prior Publication Data
US 2025/0236842 A1      Jul. 24, 2025

(30) Foreign Application Priority Data

Jun. 18, 2021    (CN) .......................... 202110682523.9

(51) Int. Cl.
*C12N 5/0786* (2010.01)
*A61K 40/00* (2025.01)
(Continued)

(52) U.S. Cl.
CPC ........ *C12N 5/0645* (2013.01); *C07K 14/7051* (2013.01); *C07K 16/2863* (2013.01);
(Continued)

(58) Field of Classification Search
None
See application file for complete search history.

(56) References Cited

U.S. PATENT DOCUMENTS 9,394,368 B2 * 7/2016 Brogdon ................ A61K 38/00
9,499,629 B2 * 11/2016 June ........................ A61P 43/00
(Continued)

FOREIGN PATENT DOCUMENTS

CN        103483453 A      1/2014
CN        203424657 U      2/2014
(Continued)

OTHER PUBLICATIONS

Bridgeman et al., CD3ζ-based chimeric antigen receptors mediate T cell activation via cis- and trans-signalling mechanisms: implications for optimization of receptor structure for adoptive cell therapy, 2013, Clinical and Experimental Immunology, vol. 175, p. 258-267 (Year: 2013).*

(Continued)

*Primary Examiner* — Christopher M Babic
*Assistant Examiner* — Hanna Marie Thueson
(74) *Attorney, Agent, or Firm* — PERRY + CURRIER INC.

(57) ABSTRACT

Provided are a macrophage-specific chimeric antigen receptor, a controllable polarized monocyte/macrophage expressing the receptor, and a preparation method and application thereof, relating to the field of biotechnology. The present disclosure provides a chimeric antigen receptor, including an extracellular antigen binding domain, a transmembrane domain, and an intracellular activation domain linked in (Continued)

sequence, wherein the extracellular antigen binding domain includes a signal peptide and/or a scFv which can specifically recognize a GBM-specifically expressed cell membrane surface protein EGFRvIII; the transmembrane domain includes a CD8α, linking an extracellular antigen binding domain and an intracellular activation domain; the intracellular activation domain includes TIR, CD3ZETA or GM-CSFRα/β, promotes the polarization of macrophage into M1 type, introduces the chimeric antigen receptor in the present disclosure into the macrophage, endows the macrophage with the function of targeting and killing the GBM, and effectively promotes and maintains the M1 polarization state of the macrophage.

7 Claims, 8 Drawing Sheets

Specification includes a Sequence Listing.

(51) Int. Cl.

| | | |
|---|---|---|
| *C07K 14/705* | (2006.01) | |
| *C07K 14/725* | (2006.01) | |
| *C07K 16/28* | (2006.01) | |
| *C12N 15/86* | (2006.01) | |

(52) U.S. Cl.
CPC .............. *C12N 15/86* (2013.01); *A61K 40/00* (2025.01); *C07K 2317/622* (2013.01); *C12N 2506/45* (2013.01); *C12N 2740/15043* (2013.01)

(56) References Cited

U.S. PATENT DOCUMENTS

| 10,780,120 | B2 * | 9/2020 | Zhao | .................. | C07K 16/2827 |
|---|---|---|---|---|---|
| 2019/0365815 | A1 * | 12/2019 | Choi | ............... | C07K 14/70521 |

FOREIGN PATENT DOCUMENTS

| CN | 103349455 | B | | 1/2016 | |
|---|---|---|---|---|---|
| CN | 106636003 | A | | 5/2017 | |
| CN | 106967685 | A | * | 7/2017 | ......... A61K 40/4204 |
| CN | 208048461 | U | | 11/2018 | |
| CN | 109266618 | A | | 1/2019 | |
| CN | 110183537 | A | | 8/2019 | |
| CN | 110564749 | A | | 12/2019 | |
| CN | 110845623 | A | | 2/2020 | |
| CN | 110904048 | A | | 3/2020 | |
| CN | 110904049 | A | | 3/2020 | |
| CN | 111138548 | A | | 5/2020 | |
| CN | 111139256 | A | | 5/2020 | |
| CN | 111518219 | A | | 8/2020 | |

OTHER PUBLICATIONS

Zhang, Li, et al. "Pluripotent stem cell-derived CAR-macrophage cells with antigen-dependent anti-cancer cell functions." Journal of hematology & oncology 13.1 (2020): 153.

Dong, Yan, et al. "Reprogramming immune cells for enhanced cancer immunotherapy: targets and strategies." Frontiers in Immunology 12 (2021): 609762.

Lei, Anhua, et al. "A chimera antigen receptor containing TLR4 signaling domain enhances CAR-iMACs polarization and potency against solid tumors.", Research Square, (2022).

* cited by examiner

SEQUENCE LISTING

```
<160> NUMBER OF SEQ ID NOS: 6

<210> SEQ ID NO 1
<211> LENGTH: 63
<212> TYPE: DNA
<213> ORGANISM: Artificial sequence
<220> FEATURE:
<223> OTHER INFORMATION: Nucleotide sequence that expresses the signal
      peptide

<400> SEQUENCE: 1
atggccttac cagtgaccgc cttgctcctg ccgctggcct tgctgctcca cgccgccagg        60
ccg                                                                      63

<210> SEQ ID NO 2
<211> LENGTH: 720
<212> TYPE: DNA
<213> ORGANISM: Artificial sequence
<220> FEATURE:
<223> OTHER INFORMATION: Nucleotide sequence that expresses sc-Fv

<400> SEQUENCE: 2
gacatccaga tgacccagag ccctagcagc ctgagcgcca gcgtgggcga cagagtgacc        60
atcacctgtc gggccagcca gggcatcaga aacaacctgg cctggtatca gcagaagccc       120
ggcaaggccc ccaagagact gatctacgct gccagcaatc tgcagagcgg cgtgcccagc       180
agattcaccg gaagcggctc cggcaccgag ttcaccctga tcgtgtccag cctgcagccc       240
gaggacttcg ccacctacta ctgcctgcag caccacagct accctctgac cagcggcgga       300
ggcaccaagg tggagatcaa gcggaccggc agcaccagcg gcagcggcaa gcctggcagc       360
```

```
ggcgagggaa gcgaggtcca ggtgctggaa tctggcggcg gactggtgca gcctggcggc    420
agcctgagac tgagctgtgc cgccagcggc ttcaccttca gcagctacgc catgtcttgg    480
gtccggcagg ctcctggaaa gggcctggaa tgggtgtccg ccatcagcgg ctctggcggc    540
tccaccaact acgccgacag cgtgaagggc cggttcacca tcagccggga caacagcaag    600
aacaccctgt atctgcagat gaacagcctg agagccgagg acaccgccgt gtactactgt    660
gccggcagca gcgggtggag cgagtactgg ggccagggca cactggtcac agtgtctagc    720

<210> SEQ ID NO 3
<211> LENGTH: 72
<212> TYPE: DNA
<213> ORGANISM: Artificial sequence
<220> FEATURE:
<223> OTHER INFORMATION: Nucleotide sequence that expresses CD8

<400> SEQUENCE: 3
atctacatct gggcgccctt ggccgggact tgtggggtcc ttctcctgtc actggttatc     60 acccttتact gc                                                         72

<210> SEQ ID NO 4
<211> LENGTH: 441
<212> TYPE: DNA
<213> ORGANISM: Artificial sequence
<220> FEATURE:
<223> OTHER INFORMATION: Nucleotide sequence that expresses TIR

<400> SEQUENCE: 4
aacatctatg atgcctttgt tatctactca agccaggatg aggactgggt aaggaatgag     60
ctagtaaaga atttagaaga aggggtgcct ccatttcagc tctgccttca ctacagagac    120
tttattcccg gtgtggccat tgctgccaac atcatccatg aaggtttcca taaaagccga    180
aaggtgattg ttgtggtgtc ccagcacttc atccagagcc gctggtgtat ctttgaatat    240
gagattgctc agacctggca gtttctgagc agtcgtgctg gtatcatctt cattgtcctg    300
cagaaggtgg agaagaccct gctcaggcag caggtggagc tgtaccgcct tctcagcagg    360
aacacttacc tggagtggga ggacagtgtc ctggggcggc acatcttctg gagacgactc    420
agaaaagccc tgctggatgg t                                              441

<210> SEQ ID NO 5
<211> LENGTH: 336
<212> TYPE: DNA
<213> ORGANISM: Artificial sequence
<220> FEATURE:
<223> OTHER INFORMATION: Nucleotide sequence that expresses CD3ZETA

<400> SEQUENCE: 5
agagtgaagt tcagcaggag cgcagacgcc cccgcgtaca agcagggcca gaaccagctc     60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga agataagat ggcggaggcc tacagtgaga ttgggatgaa aggcgagcgc    240 cggagggggca aggggcacga tggcctttac cagggtctca gtacagccac caaggacacc    300
tacgacgccc ttcacatgca ggccctgccc cctcgc                              336

<210> SEQ ID NO 6
<211> LENGTH: 1518
<212> TYPE: DNA
```

-continued

```
<213> ORGANISM: Artificial sequence
<220> FEATURE:
<223> OTHER INFORMATION: Nucleotide sequence that expresses GM-CSFR/

<400> SEQUENCE: 6
aaaaggttcc ttaggataca gcggctgttc ccgccagttc cacagatcaa agacaaactg      60
aatgataacc atgaggtgga agacgagatc atctgggagg aattcacccc agaggaaggg     120
aaaggctacc gcgaagaggt cttgaccgtg aaggaaatta ccggtggcgg tggctcgggc     180
ggtggtgggt cgggtggcgg cggatctcgc ttctgtggca tctacgggta caggctgcgc     240
agaaagtggg aggagaagat ccccaacccc agcaagagcc acctgttcca gaacgggagc     300
gcagagcttt ggcccccagg cagcatgtcg gccttcacta gcgggagtcc cccacaccag     360
gggccgtggg gcagccgctt ccctgagctg gaggggtgt tccctgtagg attcggggac     420
agcgaggtgt cacctctcac catagaggac cccaagcatg tctgtgatcc accatctggg     480
cctgacacga ctccagctgc ctcagatcta cccacagagc agccccccag cccccagcca     540
ggcccgcctg ccgcctccca cacacctgag aaacaggctt ccagctttga cttcaatggg     600
ccctacctgg ggccgcccca cagccgctcc ctacctgaca tcctgggcca gccggagccc     660
ccacaggagg gtgggagcca gaagtcccca cctccagggt ccctggagta cctgtgtctg     720
cctgctgggg ggcaggtgca actggtccct ctggcccagg cgatgggacc aggacaggcc     780
gtggaagtgg agagaaggcc gagccagggg gctgcaggga gtccctccct ggagtccggg     840
ggaggccctg cccctcctgc tcttgggcca agggtgggag gacaggacca aaaggacagc     900
cctgtggcta tacccatgag ctctggggac actgaggacc ctggagtggc ctctggttat     960
gtctcctctg cagacctggt attcacccca aactcagggg cctcgtctgt ctccctagtt    1020
ccctctctgg gcctcccctc agaccagacc cccagcttat gtcctgggct ggccagtgga    1080 cccctggag ccccaggccc tgtgaagtca gggtttgagg gctatgtgga gctccctcca    1140
attgagggcc ggtcccccag gtcaccaagg aacaatcctg tcccccctga ggccaaaagc    1200
cctgtcctga acccagggga acgcccggca gatgtgtccc caacatcccc acagcccgag    1260
ggcctccttg tcctgcagca agtgggcgac tattgcttcc tccccggcct ggggcccggc    1320
cctctctcgc tccggagtaa accttcttcc ccgggacccg gtcctgagat caagaaccta    1380
gaccaggctt ttcaagtcaa gaagccccca ggccaggctg tgcccaggt gcccgtcatt    1440 cagctcttca aagccctgaa gcagcaggac tacctgtctc tgcccccttg ggaggtcaac    1500
aagcctgggg aggtgtgt                                                  1518
```

MACROPHAGE-SPECIFIC CHIMERIC ANTIGEN RECEPTOR, CONTROLLABLE POLARIZED MONOCYTE/MACROPHAGE EXPRESSING THE RECEPTOR, AND PREPARATION METHOD AND USE THEREOF

CROSS-REFERENCE TO RELATED APPLICATION

The present application is a continuation under 35 U.S.C. § 371 of International Application No. PCT/CN2021/117808 that claims priority to Chinese Patent Application No. CN202110682523.9 filed on Jun. 18, 2021 and entitled "Macrophage-specific Chimeric Antigen Receptor, Controllable Polarized Monocyte/Macrophage Expressing the Receptor, and Preparation Method and Use thereof," the contents of which is incorporated herein by reference in its entirety.

SEQUENCE LISTING

This application contains a Sequence Listing submitted as an electronic test file named "P11229US00_Replacement_Sequence_Listing.txt", having a size in bytes of 6 kb, and created on Dec. 6, 2023. The information contained in this electronic file is hereby incorporated by reference in its entirety.

TECHNICAL FIELD

The present disclosure relates to the field of biotechnology, and in particular, to a macrophage-specific chimeric antigen receptor, a controllable polarized monocyte/macrophage expressing the receptor, and a preparation method and use thereof.

BACKGROUND ART

Glioblastoma (GBM), thought to originate from neuroglia progenitor cells, is the most prevalent and most aggressive primary brain tumor having been found at present. The incidence thereof occupies 12%-15% of intracranial tumors and 50%-60% of astrocyte tumors. Patients with the tumor have a median lifetime about 15 months, and 5-year survival rate of less than 10%. Thus, the tumor poses a great threat to human life health. Although there are means such as surgery, radiotherapy, and chemotherapy for the treatment of GBM at present, as the tumor infiltrates and grows to deep part of lobe, and has the characteristics such as rapid growth and easy recurrence, it has fewer effects, and is likely to cause secondary injury that is difficult to recover to the brain of patients.

In recent years, the tumor immune cell therapy typified by chimeric antigen receptor T cell (CAR-T) has played a more and more important role in clinical treatment for tumor, and especially exhibits better therapeutic effect in the treatment of blood cancer. Meanwhile, there are studies attempting to extend the lifetime of GBM-carrying mice by developing CAR-T targeting the GBM-specific antigen EGFRvIII. However, although a large number of explorations have been made for the CAR-T therapy in the treatment of numerous solid tumors including the GBM, the effects thereof are not ideal. The main reasons for this lie in that: 1. the off-target effect may occur in the treatment by adoptively transplanted CAR-T cells; 2. the T cells have poor infiltration to solid tumors; 3. the T cells can hardly penetrate the blood-brain barrier; and 4. the high complexity of solid tumors, the anaerobic microenvironment, and other factors cause unrecoverable depletion of cytotoxic T cells. Therefore, a new alternative immune cell treatment solution urgently needs to be found.

Macrophages, as a kind of non-specific immune cells also having the capability of killing tumor cells, are becoming a new choice for immune cell engineering as they play a central role in the interaction between the adoptive immune system and the innate immune system, have strong plasticity, are prone to breaking the blood-brain barrier, and have the property of more effectively infiltrating into the tumor tissue sites and residing for a long time. However, adoptive transplantation with macrophages has the following problems: 1. M1 type macrophages having a cellular immune function are easily polarized to M2 state under the influence of a tumor microenvironment, then lose the immune function and in turn promote the occurrence and development of tumors; 2. the conventional reinfusion treatment method by autologous cells of patients faces the problems such as few cell sources, low isolation efficiency, high reconstruction difficulty, and time and labor consuming, and the primary macrophages can hardly be genetically engineered through a route of lentiviral infection.

SUMMARY

The present disclosure provides a chimeric antigen receptor, including an extracellular antigen binding domain, a transmembrane domain, and an intracellular activation domain, which are linked in sequence, wherein the extracellular antigen binding domain includes a signal peptide and/or a scFv targeting EGFRvIII;

the transmembrane domain includes CD8α; and the intracellular activation domain includes at least one of TIR, CD3ZETA or GM-CSFRα/β.

As an optional technical solution, the signal peptide is expressed by a nucleotide sequence represented by SEQ ID NO. 1; and the scFv is expressed by a nucleotide sequence represented by SEQ ID NO. 2.

As an optional technical solution, the CD8α is expressed by a nucleotide sequence represented by SEQ ID NO. 3.

As an optional technical solution, the TIR includes an intracellular signal transduction domain derived from TLR1, TLR2, TLR3, TLR4, TLR5, TLR6, TLR7, TLR8, TLR9, TLR10, TLR13 or TLR19, wherein the intracellular signal transduction domain of TLR4 is expressed by a nucleotide sequence represented by in SEQ ID NO. 4;

the CD3ZETA is expressed by a nucleotide sequence represented by SEQ ID NO. 5; and the GM-CSFRα/β is expressed by a nucleotide sequence represented by SEQ ID NO. 6.

The present disclosure provides a polarization method of macrophage, wherein a chimeric antigen receptor is expressed in the macrophage.

The present disclosure provides a macrophage, including a chimeric antigen receptor.

The present disclosure provides a preparation method of macrophage, including steps of: constructing a lentiviral expression system containing a gene expression sequence of the chimeric antigen receptor, integrating the gene expression sequence of the chimeric antigen receptor into a pluripotent stem cell using the lentiviral expression system, and preparing the macrophage upon induced differentiation.

As an optional technical solution, the pluripotent stem cell first undergoes induced differentiation to become a monocyte, which is then differentiated into a macrophage.

The present disclosure provides a pluripotent stem cell capable of being differentiated to obtain the above macrophage, wherein the pluripotent stem cell contains a gene encoding the chimeric antigen receptor.

The present disclosure provides a monocyte capable of being differentiated to obtain the above macrophage, wherein the monocyte contains a gene encoding the chimeric antigen receptor.

The monocyte is obtained by differentiating a pluripotent stem cell.

The present disclosure provides use of a macrophage, a pluripotent stem cell or a monocyte in the preparation of a product for treating glioblastoma.

The present disclosure provides a product for treating glioblastoma, wherein the product includes the above macrophage.

The present disclosure provides a pharmaceutical agent, including the macrophage, the pluripotent stem cell or the monocyte.

In some embodiments, the pharmaceutical agent includes one or more of a pharmaceutically acceptable adjuvant, a diluent, or a carrier.

The present disclosure provides use of the chimeric antigen receptor, the macrophage, the pluripotent stem cell, the monocyte or the pharmaceutical agent in the treatment of glioblastoma.

The present disclosure provides use of the chimeric antigen receptor, the macrophage, the pluripotent stem cell, the monocyte or the pharmaceutical agent for the treatment of glioblastoma.

The present disclosure provides a method for treating glioblastoma, including:

administering a therapeutically effective amount of the macrophage, the product for treating glioblastoma or the pharmaceutical agent to a subject in need thereof.

The present disclosure provides a method for treating glioblastoma, including:

administering a therapeutically effective amount of the macrophage according to claim 5, a product for treating glioblastoma or a pharmaceutical agent to a subject in need thereof.

The present disclosure provides use of an intracellular activation domain in the preparation of a drug for treating tumor or cancer, wherein the intracellular activation domain includes at least one of TIR, CD3ZETA or GM-CSFRα/β.

In some embodiments, the drug is a macrophage; and the macrophage includes a chimeric antigen receptor containing the intracellular activation domain;

The cancer is selected from cancers related to solid tumors, and the tumors are selected from brain tumors.

In some embodiments, the cancer related to solid tumors is one selected from the group consisting of brain cancer, esophageal cancer, liver cancer, stomach cancer, intestinal cancer, lung cancer, and nasopharyngeal cancer.

In some embodiments, the brain tumor is one selected from the group consisting of glioblastoma, neurofibroma, astrocytoma, oligodendroglioblastoma, medulloblastoma, ependymoma, and pinealoma.

BRIEF DESCRIPTION OF DRAWINGS

In order to more clearly illustrate the technical solutions in embodiments of the present disclosure or in the prior art, accompanying drawings which need to be used for description of the specific embodiments or the prior art will be introduced briefly below, and apparently, the accompanying drawings in the description below merely show some embodiments of the present disclosure, and a person ordinarily skilled in the art still could obtain other drawings in light of these drawings without creative efforts.

DETAILED DESCRIPTION OF EMBODIMENTS

Figure 1:
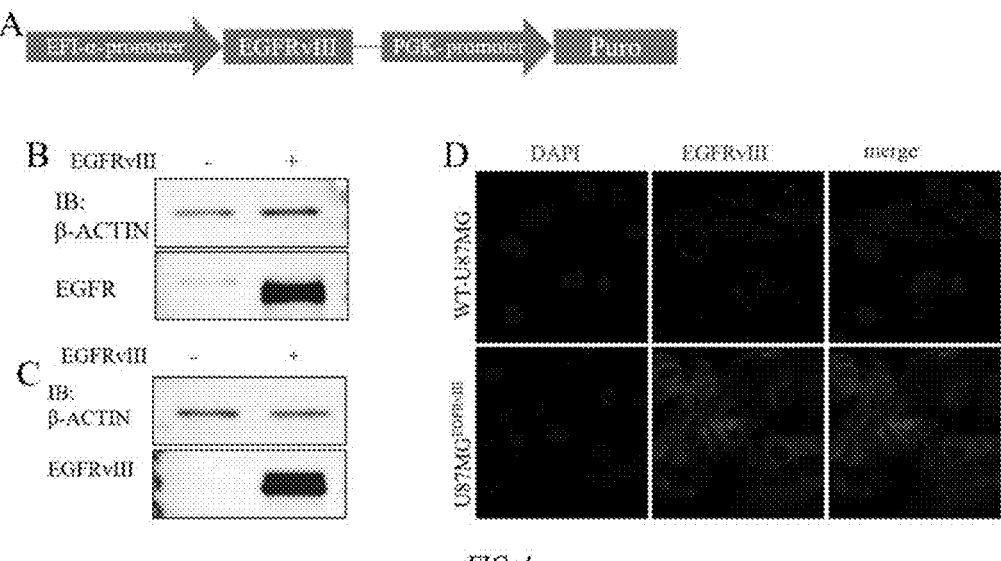
FIG. 1 shows construction of U87MG$^{EGFRvIII}$ cell line; A: constructing an EGFRvIII lentiviral expression system; B: detecting the expression level of total EGFR in U87MG cells following lentiviral infection by Western Blotting; C: detecting the expression level of total EGFRvIII in U87MG cells following lentiviral infection by Western Blotting; D: immunofluorescence detection experiment shows that EGFRvIII is located on the cell membrane surface after being over-expressed in U87MG cells.

Embodiments of the present disclosure will be described in detail below in combination with embodiments and examples, while a person skilled in the art would understand that the following embodiments and examples are merely used for illustrating the present disclosure, but should not be considered as limitation on the scope of the present disclosure. Based on the examples in the present disclosure, all of other examples obtained by a person ordinarily skilled in the art without using creative efforts shall fall within the scope of protection of the present disclosure. If no specific conditions are specified, they are carried out under normal conditions or conditions recommended by manufacturers. If manufacturers of reagents or apparatuses used are not specified, they are conventional products commercially available.

As used herein, the term "macrophage" generally refers to a myeloid immune cell developed from monocyte after exiting blood vessel, and is widely distributed in various organs of body tissues. Its main physiological role in normal tissues is: mediating specific immune responses by processing and presenting antigen; phagocytizing and degrading necrotic cells, debris, and foreign substances in a form of fixed cell or free cell, and then participating in non-specific reactions in the body; activating lymphocytes or other immune cells by secreting an inflammatory factor, thereby coordinating the inflammatory process.

As used herein, the term "chimeric antigen receptor (CAR)" generally mainly consists of three parts: an extracellular antigen binding region (antigen binding region outside the cell membrane), a transmembrane region, and an intracellular signaling region. The extracellular region is a single chain Fv domain (scFv) having a function of targeting and binding the tumor-specific antigen TAA. The transmembrane region generally consists of the immunoglobulin superfamily, such as CD8 or CD28. The intracellular signaling region mainly consists of an intracellular signal transduction domain of an activating receptor capable of activating immune cells, such as a T cell-specific co-stimulatory factor (4-1BB or CD28), and a signal activation region CD3$\zeta$. After the immune cell loaded with the chimeric antigen receptor specifically binds to the antigen on the surface of the tumor cell, the extracellular antigen binding region transmits a signal to the intracellular signal activation region, and then initiates the activation reaction of the immune cell.

As used herein, the term "polarization of macrophage" generally refers to transforming the macrophage into different functional phenotypes, i.e., classically activated macrophages M1 and alternatively activated macrophages M2 in response to various environmental factors (e.g., microbial products, damaged cells, activated lymphocytes) or in different pathophysiological conditions. Mature macrophage exhibits differentiation in phenotype and morphology, i.e. polarization phenomenon of macrophage, due to various factors. The macrophages are mainly activated to M1 and M2 two phenotypes, depending on different responses to environmental stimulation. In a long-term tumor microenvironment, M1 type is obtained through activation by signal such as IFN-$\gamma$ and LPS, mainly having the effects of suppressing tumor and enhancing immunization, and being capable of secreting inflammatory factors, chemokines, effector molecules, TNF-$\alpha$, and the like, represented by the membrane molecule CD80, surface marker CD64, etc. M2 type is obtained by activating via factors such as IL-4 and IL-13, mainly has the potential of inhibiting immune response, promoting angiogenesis, repairing tissues, promoting tumor growth, and secreting more factors such as IL-10, TGF-$\beta$, and VEGF, and is represented by the relatively high expression of CD163 and CD206.

As used herein, the term "pluripotent stem cell" is a class of multipotential cells having self-renewal and self-replication capability. In certain conditions, it can be differentiated into a plurality of types of cells, and the pluripotent stem cell (PSC) has the potential to be differentiated into multiple cell tissues, but loses the ability to develop into an intact individual, and the development potential is limited to a certain degree.

As used herein, the term "induced pluripotent stem cell (iPSC)" generally refers to a pluripotent stem cell that has the potential to be differentiated into multiple cells obtained by transferring a pluripotency factor into an adult cell and then reprogramming an initial genome expression profile.

As used herein, the term "iMAC" generally refers to macrophage subjected to induced differentiation from iPSC.

As used herein, the term "monocyte" refers to cell differentiated from hematopoietic stem cell in the bone marrow and developing in the bone marrow, which optionally can be differentiated into mature macrophage and dendritic cell. The monocyte has the characteristic of obvious deformation movement, and has the capability of phagocytizing and eliminating injured and aged cells and fragments thereof. In addition, the monocyte also participates in immune response, and transfers the antigenic determinant carried, after phagocytosis of antigen, to lymphocyte, and then induces a specific immune response of the lymphocyte. The monocyte also has the capability of recognizing and killing tumor cells.

As used herein, the term "subject" refers to a vertebrate, optionally a mammal, optionally a human. The mammal includes, but is not limited to, murine, apes, humans, domestic animals, sport animals, and pets. Tissues, cells, and progenies thereof of biological entities obtained in vivo or cultured in vitro are also included.

As used herein, the term "therapeutically effective amount" refers to an amount of agent sufficient to produce a beneficial or desired result. A therapeutically effective amount may vary depending on one or more factors of subject receiving treatment and disease condition, body weight and age of the subject, severity of disease condition, manner of administration, etc., which may be readily determined by one of ordinary skill in the art. The dosage may vary depending on one or more factors of a particular agent selected, a dosage regimen followed, combined administration with other compounds or not, administration time, a tissue to be imaged, and a physical delivery system carrying the agent.

Some embodiments of the present disclosure provide a chimeric antigen receptor, including an extracellular antigen binding domain, a transmembrane domain, and an intracellular activation domain linked in sequence.

The extracellular antigen binding domain includes a signal peptide and/or a scFv targeting EGFRvIII.

The transmembrane domain includes CD8$\alpha$.

The intracellular activation domain includes at least one of TIR, CD3ZETA or GM-CSFR$\alpha$/$\beta$.

The present disclosure provides a chimeric antigen receptor. The extracellular antigen binding domain includes a signal peptide and/or a scFv. The signal peptide can help to locate a CAR protein sequence on a cell membrane surface. The scFv can specifically recognize a cell membrane surface protein EGFRvIII specifically expressed by GBM; the transmembrane domain includes a CD8$\alpha$, linking an extracellular antigen binding domain and an intracellular activation domain; the intracellular activation domain includes TIR, CD3ZETA or GM-CSFR$\alpha$/$\beta$, promotes the polarization of macrophage into M1 type, introduces the chimeric antigen receptor provided in the present disclosure into the macrophage, enhances the immune cell to resist the immunosuppressive effect of a tumor microenvironment while endowing the macrophage with the function of targeting and killing the GBM, and effectively promotes and maintains the M1 polarization state of the macrophage.

As an optional technical solution, the signal peptide is expressed by a nucleotide sequence represented by SEQ ID NO. 1.

The scFv is expressed by a nucleotide sequence represented by SEQ ID NO. 2.

In some embodiments, the signal peptide has an amino acid sequence encoded by the nucleotide sequence represented by SEQ ID NO. 1.

In some embodiments, the scFv has an amino acid sequence encoded by the nucleotide sequence represented by SEQ ID NO. 2.

As an optional technical solution, the CD8α is expressed by a nucleotide sequence represented by SEQ ID NO. 3.

In some embodiments, the CD8α has an amino acid sequence encoded by the nucleotide sequence represented by SEQ ID NO. 3.

As an optional technical solution, the TIR includes, but is not limited to, an intracellular signal transduction domain derived from TLR1, TLR2, TLR3, TLR4, TLR5, TLR6, TLR7, TLR8, TLR9, TLR10, TLR13 or TLR19.

The intracellular signal transduction domain of the TLR4 is expressed by a nucleotide sequence represented by in SEQ ID NO. 4.

The CD3ZETA is expressed by a nucleotide sequence represented by SEQ ID NO. 5.

The GM-CSFRα/β is expressed by a nucleotide sequence represented by SEQ ID NO. 6.

In some embodiments, the intracellular signal transduction domain of the TLR4 has an amino acid sequence encoded by the nucleotide sequence represented by SEQ ID NO. 4.

In some embodiments, the CD3ZETA has an amino acid sequence encoded by the nucleotide sequence represented by SEQ ID NO. 5.

In some embodiments, the GM-CSFRα/β has an amino acid sequence encoded by the nucleotide sequence represented by SEQ ID NO. 6.

Some embodiments of the present disclosure provide a polarization method of macrophage, wherein a chimeric antigen receptor is expressed in the macrophage.

In the present disclosure, the M1 polarization of macrophage is realized by expressing the above chimeric antigen receptor in the macrophage, and the method is simple and effective.

Some embodiments of the present disclosure provide a macrophage, including a chimeric antigen receptor.

The macrophage can express the above chimeric antigen receptor provided in the present disclosure, can maintain the M1 polarization state, and has strong targeted killing property to GBM.

Figure 9:
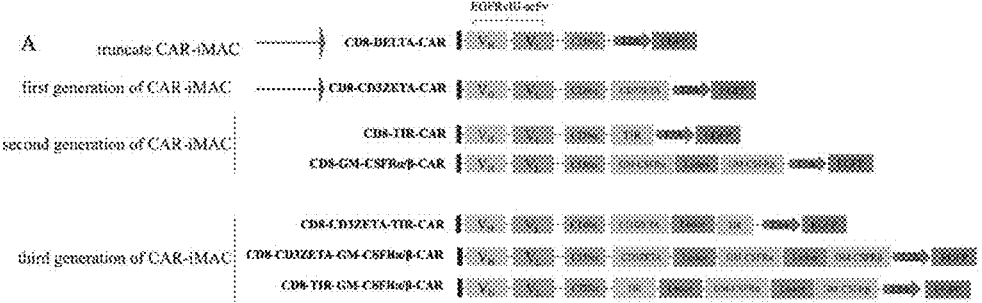
FIG. 9 shows structural schematic diagrams of three generations of CARs designed in the present disclosure, and comparative schematic diagrams of immune activation of different CAR-iMACs depending on CAR.
Figure 9:
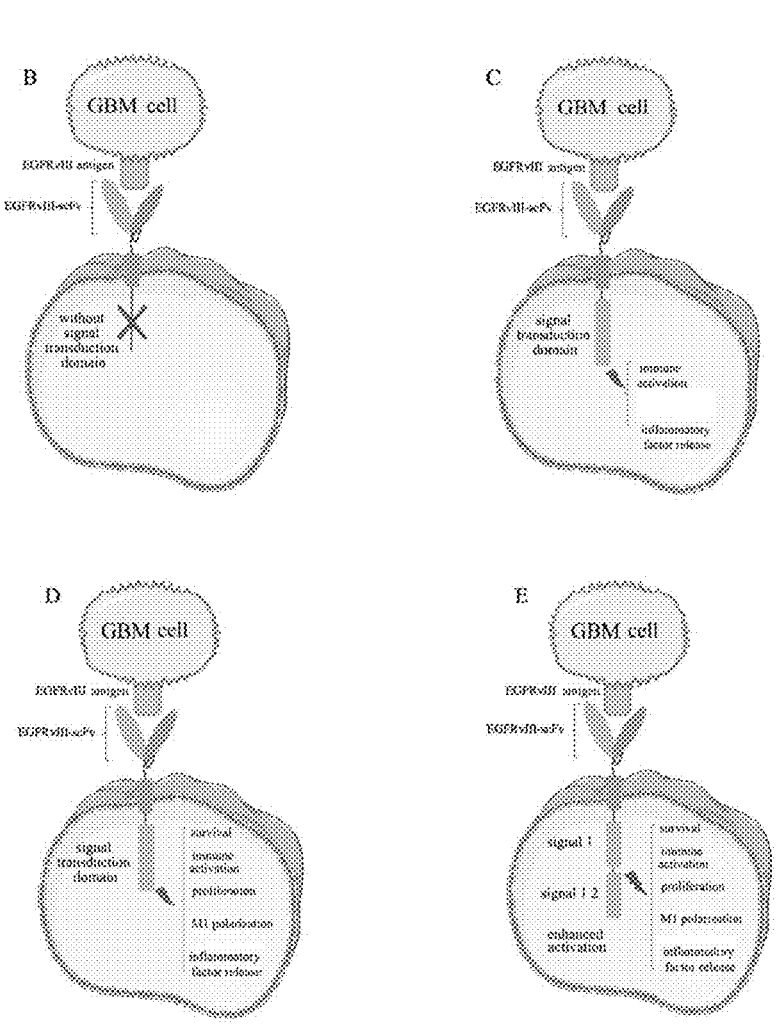

A structural schematic diagrams of three generations of CARs designed in the present disclosure, and comparative schematic diagrams of immune activation of different CAR-iMACs depending on CAR are as shown in FIG. 9.

A in FIG. 9 shows that Truncate CAR mainly consists of the scFv domain extracellularly specifically recognizing the EGFRvIII protein and the CD8α transmembrane domain. An intracellular signal transduction domain is lacked. The first generation of CAR mainly consists of the scFv domain extracellularly specifically recognizing the EGFRvIII protein, the CD8α transmembrane domain, and an intracellular CD3ZETA signal transduction domain. The second generation of CAR mainly consists of the scFv domain extracellularly specifically recognizing the EGFRvIII protein, the CD8α transmembrane domain, and an intracellular signal transduction domain specific to macrophage. The intracellular signal transduction domain is a single TIR or GM-CSFRα/β activation domain, respectively. The third generation of CAR is upgraded from the second generation of CAR. The difference lies in that the intracellular signal transduction domain of the third generation of CAR is formed by combining CD3ZETA, TIR, and GM-CSFRα/β with each other through a Linker, respectively, so as to achieve a stronger and more durable immune activation effect.

B-E in FIG. 9 show schematic diagrams of immune activation of different CAR-iMACs depending on CAR. Due to the lack of intracellular signal transduction domain, Truncate CAR-iMAC does not have the function of immune activation by means of CAR. After the extracellular scFv of the first generation of CAR targetedly recognizes EGFRvIII, the intracellular CD3ZETA signal transduction domain thereof is activated, further initiating the immune activation of the first generation of CAR-iMAC and releasing a small amount of inflammatory factor. Activation of TIR can stimulate macrophage immune activation, so as to release inflammatory factors such as IL1, IL6, and TNFα, and polarize to M1 type. Activation of GM-CSFRα/β can promote mass amplification of macrophages, and immune activation, so as to release inflammatory factors such as IL12, IL23, and TNFα, and polarize to M1 type. Therefore, compared with the first generation of CAR-iMAC, the second generation of CAR-iMAC, after targeting EGFRvIII, significantly improves the anti-tumor capabilities such as survival amplification, M1 polarization, and immune activation in a tumor microenvironment. When the extracellular scFv of the third generation of CAR targetedly recognizes EGFRvIII, 2 signal transduction domains in TIR, CD3ZETA, and GM-CSFRα/β in the cell will synergistically play a role of immune activation, may utilize the advantages of different immune activation signal paths, and further play a stronger and more durable immune activation effect.

Some embodiments of the present disclosure provide a preparation method of macrophage, including steps of: constructing a lentiviral expression system containing a gene expression sequence of the chimeric antigen receptor, integrating the gene expression sequence of the chimeric antigen receptor into a pluripotent stem cell using the lentiviral expression system, and preparing the macrophage upon induced differentiation.

As an optional technical solution, the pluripotent stem cell first undergoes induced differentiation to become a monocyte, which is then differentiated into a macrophage.

The inventors found through researches that the primary macrophages are difficult to be infected by lentiviruses, and can hardly be edited and engineered. Based on this, the present disclosure provides a preparation method of the above macrophage, and the macrophage prepared by the method of the present disclosure can stably over-express the chimeric antigen receptor for a long time, and can solve the problems such as low editing efficiency, long cycle, heavy workload, and delayed treatment in current immune cell therapy.

Some embodiments of the present disclosure provide a pluripotent stem cell capable of being differentiated to obtain the above macrophage, wherein the pluripotent stem cell contains a gene encoding the chimeric antigen receptor.

As the pluripotent stem cell contains the gene encoding the above chimeric antigen receptor, the state of the pluripotent stem cell is more prone to the M1 state pro-inflammatory and suppressing tumor, and the pluripotent stem cell can be optionally differentiated to obtain the macrophage, which is more favorable for suppressing the tumor.

Some embodiments of the present disclosure provide a monocyte capable of being differentiated to obtain the above macrophage, wherein the monocyte contains a gene encoding the chimeric antigen receptor.

The monocyte is obtained by differentiating a pluripotent stem cell.

Some embodiments of the present disclosure provide use of a macrophage, a pluripotent stem cell or a monocyte in the preparation of a product for the treatment of glioblastoma.

As the macrophage provided in the present disclosure can maintain the M1 polarization state and has strong targeted killing property to GBM, the macrophage can be used for preparing a product for the treatment of glioblastoma, and the pluripotent stem cell, which can be differentiated to obtain the above macrophage, can also be used for preparing a product for the treatment of glioblastoma.

Some embodiments of the present disclosure provide a product for the treatment of glioblastoma, wherein the product includes the above macrophage.

The macrophage provided in the present disclosure can maintain the M1 polarization state, and has strong targeted killing property to GBM, and the product including the macrophage also has the effect of treating glioblastoma.

Some embodiments of the present disclosure provide a pharmaceutical agent, including the macrophage, the pluripotent stem cell or the monocyte.

In some embodiments, the pharmaceutical agent includes one or more of a pharmaceutically acceptable adjuvant, a diluent, or a carrier.

Some embodiments of the present disclosure provide use of the chimeric antigen receptor, the macrophage, the pluripotent stem cell, the monocyte or the pharmaceutical agent in the treatment of glioblastoma.

Some embodiments of the present disclosure provide use of the chimeric antigen receptor, the macrophage, the pluripotent stem cell, the monocyte or the pharmaceutical agent for the treatment of glioblastoma.

Some embodiments of the present disclosure provide a method for treating glioblastoma, including:

administering a therapeutically effective amount of the macrophage, the product or the pharmaceutical agent for the treatment of glioblastoma to a subject in need thereof.

Some embodiments of the present disclosure provide use of an intracellular activation domain for the preparation of a drug for the treatment of tumor or cancer, wherein the intracellular activation domain includes at least one of TIR, CD3ZETA or GM-CSFRα/β.

In some embodiments, the drug is a macrophage; and the macrophage includes a chimeric antigen receptor containing the intracellular activation domain; and the cancer is selected from cancers related to solid tumors, and the tumors are selected from brain tumors.

In some embodiments, the cancers related to solid tumors are one selected from brain cancer, esophageal cancer, liver cancer, stomach cancer, intestinal cancer, lung cancer, and nasopharyngeal cancer.

In some embodiments, the brain tumor is one selected from the group consisting of glioblastoma, neurofibroma, astrocytoma, oligodendroglioblastoma, medulloblastoma, ependymoma, pinealoma and so on.

The intracellular activation domain in the present disclosure can be widely applied to various macrophages targeting other tumor antigens, has wide applicability, may effectively activate the macrophages, and promotes the macrophages to polarize towards the immune activation direction.

The present disclosure provides a macrophage-specific chimeric antigen receptor, including an extracellular antigen binding domain, a transmembrane domain, and an intracellular activation domain linked in sequence. In the above, the extracellular antigen binding domain includes a signal peptide and/or a scFv, wherein the signal peptide can help to locate a CAR protein sequence on a cell membrane surface. The scFv can specifically recognize a specifically expressed cell membrane surface protein EGFRvIII in GBM; the transmembrane domain includes a CD8α, linking an extracellular antigen binding domain and an intracellular activation domain; the intracellular activation domain includes at least one of TIR, CD3ZETA or GM-CSFRα/β, and the intracellular activation domain in the present disclosure is a macrophage-specific intracellular activation domain, may effectively activate the macrophage, and promote the polarization of the macrophage to the immune activation direction, i.e., promote the polarization of the macrophage to M1 type; in addition, the intracellular activation domain in the present disclosure has wide applicability to macrophages targeting other tumor antigens, and the above planned effect can be realized. At the same time, the GM-CSFRα/β domain may effectively maintain the monocyte-like state of the macrophage. This state is favorable for infiltration of macrophage into the tumor tissue. The chimeric antigen receptor provided in the present disclosure is introduced into the macrophage, the immune cell is also enhanced to resist the immunosuppressive effect of a tumor microenvironment while the macrophage is endowed with the function of targeting and killing the GBM, and the M1 polarization state of the macrophage is effectively promoted and maintained.

The chimeric antigen receptor provided in the present disclosure can endow the macrophage with the property of targeting GBM, reduce off-target effect, promote and maintain the M1 polarization state of the macrophage in a tumor microenvironment, and improve killing efficiency of the macrophage. The polarization method of macrophage provided in the present disclosure is simple, and can realize M1 polarization of the macrophage. The macrophage provided in the present disclosure can solve at least one of the above problems.

In the polarization method of macrophage provided in the present disclosure, the M1 polarization of macrophage is realized by expressing the above chimeric antigen receptor in the macrophage, and the method is simple and effective.

The macrophage provided in the present disclosure can express the above chimeric antigen receptor provided in the present disclosure, can maintain the M1 polarization state, and has strong targeted killing property to GBM.

The inventors found through researches that the primary macrophages are difficult to be infected by lentiviruses, and can hardly be edited and engineered. Based on this, the present disclosure provides a preparation method of the above macrophage, including: constructing a lentiviral expression system containing a gene expression sequence of the chimeric antigen receptor, integrating the gene expression sequence of the chimeric antigen receptor into a pluripotent stem cell using the lentiviral expression system, and preparing the macrophage upon induced differentiation. The macrophage can stably over-express the chimeric antigen receptor for a long time, and can solve the problems such as low editing efficiency, long cycle, heavy workload, and delayed treatment in current immune cell therapy.

The pluripotent stem cell provided in the present disclosure contains the gene encoding the above chimeric antigen receptor, the state of the pluripotent stem cell is more prone to the M1 state pro-inflammatory and suppressing tumor, and the pluripotent stem cell can be optionally differentiated to obtain the macrophage, which is more favorable for suppressing the tumor.

The present disclosure is described below through examples and control examples. However, it should be understood that these examples are merely for more detailed description, but should not be construed as limiting the present disclosure in any form.

EXAMPLES

Example 1

Constructing a GBM cell line expressing EGFRvIII antigen.

An expression sequence of GBM-specific membrane protein EGFRvIII was obtained, and was cloned into a lentivirus expression plasmid Lenti-EF1A-PGK-Puro by means of molecular cloning. The EGFRvIII lentivirus expression system constructed is as shown in A in FIG. 1. GBM-specific membrane protein EGFRvIII was expressed in GBM cell lines U87MG and LN-229, respectively (preserved by Liuchong subject group of Zhejiang University School of Medicine) by means of the lentivirus expression system, to obtain a U87MG$^{EGFRvIII}$ cell line stably expressing the membrane protein.

Expression levels of total EGFR and EGFRvIII in U87MG cells after lentivirus infection were respectively detected by Western Blotting, with following experimental steps.

1. Preparation of Cell Total Protein Sample
    (1) Wild-type U87MG cells and U87MG cells overexpressing EGFRvIII through lentivirus were inoculated into a 6CM cell culture dishes, and cultured in a 37° C./5% $CO_2$ cell incubator until overgrowing on the culture dishes.
    (2) Cell culture solution was discarded with a pipette. To each culture dish 3 ml of pre-cooled 4° C. 1×PBS (0.01 M pH7.2~7.3) was added. The culture dishes were laid flat and gently shaken for 1 min to wash the cells, and then washing liquid was discarded. The above operations were repeated twice, and the cells were washed three times in total to wash out the culture solution. After the PBS was discarded completely, the culture dishes were placed on ice.
    (3) To each cell culture dish 500 µl of RIPA lysis solution containing protease inhibitor was added, for lysis on ice for 30 min, and to sufficiently lyse the cells, the culture dishes should be gently shaken on a shaker.
    (4) After the lysis was completed, the cells were scraped with a clean scraper to one side of a culture flask (act fast), then the cell debris and lysis solution were transferred to a 1.5 ml centrifuge tube with a pipette.
    (5) The resultant was centrifuged at 12000 rpm at 4° C. for 20 min.
    (6) Supernatant after the centrifugation was separated and transferred to new 1.5 ml centrifuge tubes.
    (7) To the cell lysis solution obtained in the previous step, 5×SDS loading buffer having a final use concentration of 1× and containing β-mercaptoethanol was added. After being mixed well, the mixture was heated in a 95° C. metal bath for 5 minutes to denature the protein. The resultant was stored at −20° C. or on ice for subsequent use.

2. SDS Gel Electrophoresis and Transmembrane
    (8) A gel electrophoresis system was prepared, and 10 µl of each protein sample obtained in the previous step and 5 µl of protein marker (marker) were added to corresponding loading holes.
    (9) The electrophoresis condition was set to be 100 V constant voltage, and the electrophoresis was terminated when bromophenol blue just appeared, and the transmembrane was performed.
    (10) The gel obtained in the previous step was placed in a wet transmembrane system, and subjected to electrotransformation for about 120 minutes in a 100 V constant pressure condition, so as to sufficiently transfer the protein in the gel onto a PVDF membrane.
3. Immunoreaction
    (11) The PVDF membrane transferred with protein in the previous step was quickly taken out, and placed in the TBST solution to wash out a transfer buffer, then moved into 5% skimmed milk formulated with TBST, and sealed at room temperature for 1 hour. During this period, it should be gently shaken on a horizontal shaker.
    (12) A position of target protein (EGFRvIII, EFGR, and internal reference β-ACTIN) was predicted through identification of the protein marker on PVDF, and the membranes containing the target protein were cut into appropriate sizes with scissors, respectively.
    (13) The membranes containing the target protein obtained in the above were placed in 5% skimmed milk containing EGFRvIII, EFGR, and β-ACTIN primary antibody, respectively, and incubated overnight at 4° C. (10-12 hours).
    (14) The PVDF membrane incubated with primary antibody was taken out from the previous step, and washed with TBST three times, 10 minutes each time, on the horizontal shaker at room temperature.
    (15) According to the species matching principle, the PVDF membrane washed in the previous step was placed in 5% skimmed milk diluting a secondary antibody in the same species source and conjugated with HRP, and incubated on the shaker at room temperature for 1 hour.
    (16) The PVDF membrane incubated with primary antibody was taken out from the previous step, and washed with TBST three times, 10 minutes each time, on the horizontal shaker at room temperature.
4. Chemical Imaging
    (17) The TBST on the PVDF membrane washed in the previous step was dried with absorbent paper, and the PVDF membrane was placed in a chemiluminescent imager with front side up. An appropriate amount of ECL chemiluminescent solution pre-formulated was added to the front side of the membrane with a pipette quickly. After imaging conditions were set, imaging was performed and an image was saved.

Results are as shown in B in FIG. 1 and C in FIG. 1, indicating that EGFR and EGFRvIII are highly expressed in the constructed U87MG$^{EGFRvIII}$ cell line.

The immunofluorescence experimental steps were as follows:

Day 1:
    1. Wild-type U87MG cells and U87MG cells over-expressing EGFRvIII by lentivirus were inoculated into 24-well cell culture plates paved with cell slide.
    2. The cells were cultured in a 37° C./5% $CO_2$ cell incubator for 12 hours.

Day 2:

3. In the culture plate, slide already with the cells was washed by PBS 3 times, 3 min each time.
4. The cell slide was fixed with 4% paraformaldehyde for 15 min, and washed by PBS 3 times, 3 min each time.
5. Permeating with 0.5% Triton X-100 (formulated by PBS) was performed at room temperature for 20 min (this step was omitted for antigen expressed on cell membrane).
6. The slide was washed by PBS 3 times, 3 min each time, the PBS was sucked dry with absorbent paper, 2.5% BSA was dropped on the slide, and the slide was sealed at room temperature for 30 min (or at 37° C. for 20 min).
7. A sealing liquid was sucked dry with absorbent paper, without washing, and to each slide a sufficient amount of diluted EGFRvIII primary antibody was dropped; and the slide was placed in a wet box, incubated at 4° C. overnight (generally greater than 18 hours), or at 37° C. for 1-2 hours.

Day 3:

8. Adding fluorescent secondary antibody: the cell slide was washed by PBST 3 times, 3 min each time, and after excessive liquid on the cell slide was sucked dry by the absorbent paper, diluted fluorescence secondary antibody was dropped, the resultant was incubated at 20-37° C. in a wet box for 1 h, and slices were washed by PBST 3 times, 3 min each time. Note: from the addition of fluorescent secondary antibody, all the following operation steps were performed in dark as much as possible.
9. Re-staining nucleus: DAPI was dropped for incubation in light-tight condition for 5 min, the nucleus of specimen was stained, excessive DAPI was washed away by PBST for 5 min×4 times, the liquid on the cell slide was sucked dry with the absorbent paper, and the slices were sealed with a sealing liquid containing an anti-fluorescence quenching agent, and then the slices were observed and an image was captured under a fluorescence microscope.

Immunofluorescence detection experiments showed that EGFRvIII, after being over-expressed in U87MG cells, was positioned on the cell membrane surface (D in FIG. 1).

Example 2

Constructing CAR-iMAC, and investigating its targeted killing function on GBM cell line through in vitro experiments.

1. Constructing a Method of Making iPSC Undergo Induced Differentiation to Become iMAC 1) Reprogramming PBMC (Peripheral Blood Mononuclear Cell) to iPSC PBMCs were isolated from fresh blood, with the advantages of a large number and easy acquisition, are a preferable material for inducing to obtain iPSC. After the PBMC was obtained by separation, expression vectors expressing five transcription factors OCT3/4, SOX2, KLF4, L-MYC, and LIN28A were transfected into PBMC by electrotransformation method, to induce reprogramming thereof, and finally iPSC was obtained.

2) Experimental Steps of Inducing iPSC to be Differentiated into Monocyte (iMONO) and M1-Type Macrophage (iMAC) Based on Embryoid Body (EB) Formation were as Follows:

1. EB formation (day 0). When iPSC was cultured to an area covering 60-80% of the culture dish, it was digested with versene into individual cells or smaller cell clumps. After centrifugation at 600 rpm for 3 min, the resultant was resuspended with mTeSR1 medium containing Y-27632, and inoculated into low-adsorption six-well plates at a ratio of 1:2 or 1:3. In a 37° C./5% $CO_2$ incubator, incubation was performed on the shaker for about 24 hours. Then EB might be formed.

2. Primitive streak and mesoderm induction (day 1). Medium for culturing EB in step 1 was removed. MI medium (APEL II medium+10 ng/mL BMP4+5 ng/mL bFGF) was added. Culturing was continued for 24 hours in the conditions of step 1.

3. Hematopoietic stem cell (HSC) induction (days 2-7). MI medium in step 2 was removed. HS medium (APEL II medium+10 ng/mL BMP4+5 ng/mL bFGF+50 ng/ml VEGF+100 ng/mL SCF) was added. Culturing was continued in the conditions of step 1.

4. Myeloid cell and mononuclear precursor cell (MPC) amplification (days 8-10). HS medium in step 3 was removed. ME-1 medium (APEL II medium+5 ng/mL bFGF+50 ng/mL VEGF+100 ng/mL SCF+10 ng/mL IGF1+25 ng/mL IL-3+50 ng/mL M-CSF+50 ng/mL GM-CSF (granulocyte-macrophage colony stimulating factor)) was added. Culturing was continued under in conditions of step 1.

5. Induction of MONO (about day 11). The EB in step 4 was transferred to Matrigel-coated six-well plates. ME-2 medium (StemSpan-XF medium+5 ng/mL bFGF+50 ng/ml VEGF+100 ng/mL SCF+10 ng/mL IGF1+25 ng/mL IL-3+50 ng/mL M-CSF+50 ng/mL GM-CSF) was added, and culturing was performed stationarily in a 37° C./5% $CO_2$ incubator. During this period of time, MONO in a single cell state would continue to float in the medium. The fluid was changed and iMONOs were collected by centrifugation.

6. Maturation of iMAC (about day 17). The iMONOs collected in step 5 were collected into new Matrigel-coated six-well plates. MM medium (StemSpan-XF medium+5 ng/mL bFGF+50 ng/ml VEGF+100 ng/mL SCF+10 ng/mL IGF1+25 ng/mL IL-3+100 ng/mL M-CSF+100 ng/mL GM-CSF) was added, and culturing was performed stationarily in a 37° C./5% $CO_2$ incubator. During this period of time, MONO of a smaller volume was seen to mature into vacuolated iMAC of a larger volume.

7. M1 polarization of iMAC. The mature iMACs in step 6 were collected, and MS medium (RPMI1640+100 ng/mL M-CSF+100 ng/mL GM-CSF) containing 100 ng/mL LPS and 100 ng/mL IFN-γ was added to obtain polarized iMAC after about 24 hours.

This process only requires 13-28 days for induced differentiation. During this period of time, iMONOs and iMACs were produced continuously. Thus, iMONOs and iMACs with high differentiation efficiency and good activity provide a guarantee for subsequent need of a large number of immune cells.

3) Inspecting the Property of Macrophage of iMAC Derived from iPSC

An iMAC surface marker antigen was detected by flow analysis technology, iMAC gene expression profiles were analyzed by single cell RNA-seq technology, and it was determined that iPSC was successfully induced and differentiated into M1 type iMAC by detecting cytokine secretion by ELISA technology and other methods.

2. Constructing CAR-iMONO or CAR-iMAC Having a Function of Targeting GBM

1) Designing a Chimeric Antigen Receptor Specifically Recognizing EGFRvIII

A gene expression sequence of sc-Fv targeting EGFRvIII was acquired. This sequence, by molecular cloning method, was cloned with a transmembrane domain gene expression sequence of CD8α and expression sequences of TIR and CD3ZETA domains into lentivirus expression plasmid Lenti-EF1A-T2A-EGFP-Puro in a combined manner, to form a fusion expressed CAR sequence (A in FIG. 2). Meanwhile, CAR (scFv-CD8-DELTA-CAR) without an intracellular activation domain was simulated as a negative control to check whether the intracellular signal transduction domain can exert the immune activation function.

In the above, the signal peptide is a short peptide chain containing a hydrophobic amino acid sequence, and has the function of guiding the newly synthesized protein to cross the membrane or secret out of the cell. The expression sequence of the signal peptide is expressed by the nucleic acid sequence represented by SEQ ID NO. 1:

```
                              (SEQ ID NO. 1)
ATGGCCTTACCAGTGACCGCCTTGCTCCTGCCGCTGGCCTTGCTGCT

CCACGCCGCCAGGCCG.
```

The expression sequence of sc-Fv is expressed by the nucleotide sequence represented by SEQ ID NO. 2.

In one or more embodiments, the sc-Fv has an amino acid sequence encoded by the nucleotide sequence represented by SEQ ID NO. 2:

```
                              (SEQ ID NO. 2)
GACATCCAGATGACCCAGAGCCCTAGCAGCCTGAGCGCCAGCGTGGG

CGACAGAGTGACCATCACCTGTCGGGCCAGCCAGGGCATCAGAAACAA

CCTGGCCTGGTATCAGCAGAAGCCCGGCAAGGCCCCCAAGAGACTGAT

CTACGCTGCCAGCAATCTGCAGAGCGGCGTGCCCAGCAGATTCACCGG

AAGCGGCTCCGGCACCGAGTTCACCCTGATCGTGTCCAGCCTGCAGCC

CGAGGACTTCGCCACCTACTACTGCCTGCAGCACCACAGCTACCCTCTG

ACCAGCGGCGGAGGCACCAAGGTGGAGATCAAGCGGACCGGCAGCAC

CAGCGGCAGCGGCAAGCCTGGCAGCGGCGAGGGAAGCGAGGTCCAGG

TGCTGGAATCTGGCGGCGGACTGGTGCAGCCTGGCGGCAGCCTGAGAC

TGAGCTGTGCCGCCAGCGGCTTCACCTTCAGCAGCTACGCCATGTCTTG

GGTCCGGCAGGCTCCTGGAAAGGGCCTGGAATGGGTGTCCGCCATCAG

CGGCTCTGGCGGCTCCACCAACTACGCCGACAGCGTGAAGGGCCGGTT

CACCATCAGCCGGGACAACAGCAAGAACACCCTGTATCTGCAGATGAAC

AGCCTGAGAGCCGAGGACACCGCCGTGTACTACTGTGCCGGCAGCAGC

GGGTGGAGCGAGTACTGGGGCCAGGGCACACTGGTCACAGTGTCTAGC.
```

The CD8α is expressed by the nucleotide sequence represented by SEQ ID NO. 3.

In one or more embodiments, the CD8α has an amino acid sequence encoded by the nucleotide sequence represented by SEQ ID NO. 3:

```
                              (SEQ ID NO. 3)
ATCTACATCTGGGCGCCCTTGGCCGGGACTTGTGGGGTCCTTCTCCT

GTCACTGGTTATCACCCTTTACTGC.
```

The TIR is expressed by the nucleotide sequence represented by SEQ ID NO. 4.

In one or more embodiments, the TIR has an amino acid sequence encoded by the nucleotide sequence represented by SEQ ID NO. 4:

```
                              (SEQ ID NO. 4)
AACATCTATGATGCCTTTGTTATCTACTCAAGCCAGGATGAGGACTGG

GTAAGGAATGAGCTAGTAAAGAATTTAGAAGAAGGGGTGCCTCCATTTCA

GCTCTGCCTTCACTACAGAGACTTTATTCCCGGTGTGGCCATTGCTGCCA

ACATCATCCATGAAGGTTTCCATAAAAGCCGAAAGGTGATTGTTGTGGTG

TCCCAGCACTTCATCCAGAGCCGCTGGTGTATCTTTGAATATGAGATTGC

TCAGACCTGGCAGTTTCTGAGCAGTCGTGCTGGTATCATCTTCATTGTCC

TGCAGAAGGTGGAGAAGACCCTGCTCAGGCAGCAGGTGGAGCTGTACC

GCCTTCTCAGCAGGAACACTTACCTGGAGTGGGAGGACAGTGTCCTGG

GGCGGCACATCTTCTGGAGACGACTCAGAAAAGCCCTGCTGGATGGT.
```

The CD3ZETA is expressed by the nucleotide sequence represented by SEQ ID NO. 5.

In one or more embodiments, the CD3ZETA has an amino acid sequence encoded by the nucleotide sequence represented by SEQ ID NO. 5:

```
                              (SEQ ID NO. 5)
AGAGTGAAGTTCAGCAGGAGCGCAGACGCCCCCGCGTACAAGCAGG

GCCAGAACCAGCTCTATAACGAGCTCAATCTAGGACGAAGAGAGGAGTA

CGATGTTTTGGACAAGAGACGTGGCCGGGACCCTGAGATGGGGGGAAA

GCCGAGAAGGAAGAACCCTCAGGAAGGCCTGTACAATGAACTGCAGAAA

GATAAGATGGCGGAGGCCTACAGTGAGATTGGGATGAAAGGCGAGCGC

CGGAGGGGCAAGGGGCACGATGGCCTTTACCAGGGTCTCAGTACAGCC

ACCAAGGACACCTACGACGCCCTTCACATGCAGGCCCTGCCCCCTCGC.
```

The GM-CSFRα/β is expressed by the nucleotide sequence represented by SEQ ID NO. 6.

In one or more embodiments, the GM-CSFRα/β has an amino acid sequence encoded by the nucleotide sequence represented by SEQ ID NO. 6:

```
                              (SEQ ID NO. 6)
AAAAGGTTCCTTAGGATACAGCGGCTGTTCCCGCCAGTTCCACAGATC

AAAGACAAACTGAATGATAACCATGAGGTGGAAGACGAGATCATCTGGG

AGGAATTCACCCCAGAGGAAGGGAAAGGCTACCGCGAAGAGGTCTTGA

CCGTGAAGGAAATTACCGGTGGCGGTGGCTCGGGCGGTGGTGGGTCG

GGTGGCGGCGGATCTCGCTTCTGTGGCATCTACGGGTACAGGCTGCGC
```

US 12,668,780 B2

17                                                                  18

-continued

AGAAAGTGGGAGGAGAAGATCCCCAACCCCAGCAAGAGCCACCTGTTC

CAGAACGGGAGCGCAGAGCTTTGGCCCCCAGGCAGCATGTCGGCCTTC

ACTAGCGGGAGTCCCCCACACCAGGGGCCGTGGGGCAGCCGCTTCCCT

GAGCTGGAGGGGGTGTTCCCTGTAGGATTCGGGGACAGCGAGGTGTCA

CCTCTCACCATAGAGGACCCCAAGCATGTCTGTGATCCACCATCTGGGC

CTGACACGACTCCAGCTGCCTCAGATCTACCCACAGAGCAGCCCCCCAG

CCCCCAGCCAGGCCCGCCTGCCGCCTCCCACACACCTGAGAAACAGGC

TTCCAGCTTTGACTTCAATGGGCCCTACCTGGGGCCGCCCCACAGCCGC

TCCCTACCTGACATCCTGGGCCAGCCGGAGCCCCCACAGGAGGGTGGG

AGCCAGAAGTCCCCACCTCCAGGGTCCCTGGAGTACCTGTGTCTGCCTG

CTGGGGGGCAGGTGCAACTGGTCCCTCTGGCCCAGGCGATGGGACCAG

GACAGGCCGTGGAAGTGGAGAGAAGGCCGAGCCAGGGGGCTGCAGGG

AGTCCCTCCCTGGAGTCCGGGGGAGGCCCTGCCCCTCCTGCTCTTGGG

CCAAGGGTGGGAGGACAGGACCAAAAGGACAGCCCTGTGGCTATACCC

ATGAGCTCTGGGGACACTGAGGACCCTGGAGTGGCCTCTGGTTATGTCT

CCTCTGCAGACCTGGTATTCACCCCAAACTCAGGGGCCTCGTCTGTCTC

CCTAGTTCCCTCTCTGGGCCTCCCCTCAGACCAGACCCCCAGCTTATGT

CCTGGGCTGGCCAGTGGACCCCCTGGAGCCCCAGGCCCTGTGAAGTCA

GGGTTTGAGGGCTATGTGGAGCTCCCTCCAATTGAGGGCCGGTCCCCC

AGGTCACCAAGGAACAATCCTGTCCCCCCTGAGGCCAAAAGCCCTGTCC

TGAACCCAGGGGAACGCCCGGCAGATGTGTCCCCAACATCCCCACAGC

CCGAGGGCCTCCTTGTCCTGCAGCAAGTGGGCGACTATTGCTTCCTCCC

CGGCCTGGGGCCCGGCCCTCTCTCGCTCCGGAGTAAACCTTCTTCCCC

GGGACCCGGTCCTGAGATCAAGAACCTAGACCAGGCTTTTCAAGTCAAG

AAGCCCCCAGGCCAGGCTGTGCCCCAGGTGCCCGTCATTCAGCTCTTCA

AAGCCCTGAAGCAGCAGGACTACCTGTCTCTGCCCCCTTGGGAGGTCAA

CAAGCCTGGGGAGGTGTGT.

2) Constructing CAR-iMONO or CAR-iMAC

Expression sequences of three different CARs were integrated into iPSC using the lentiviral system, respectively. A cell line stably expressing CAR (CAR-iPSC) was obtained by technological means such as green fluorescence expression and single cell RNA-seq. Thereafter, the three kinds of CAR-iPSCs were induced and differentiated into CAR-iMONO or CAR-iMAC activated depending on CAR.

Experimental steps of constructing CAR-iMAC, and performing a non-specific basic phagocytosis function test were as follows:

1. A certain number of CAR-iMACs expressing green fluorescent protein were inoculated into six-well plates, and the resultant was polarized in RPMI 1640 medium containing 100 ng/ml LPS, 100 ng/ml humanized INF-γ (γ interferon), 100 ng/ml M-CSF (macrophage colony stimulating factor), and 100 ng/ml GM-CSF for 24 hours, in a 37° C./5% $CO_2$ cell incubator.
  2. The polarized CAR-iMAC obtained above and wild-type LN-229 cells expressing erythrosine (tdTomato) red fluorescent protein, at a 10/1 ratio, were inoculated into a glass dish, and the resultant underwent co-culturing with RPMI1640 culture medium containing 100 ng/ml M-CSF and 100 ng/ml GM-CSF in a 37° C./5% $CO_2$ cell incubator for 24 hours.
  3. The glass dish in the previous step was placed in a confocal fluorescence scanning microscope, and after setting the parameters, co-positioning situation of red fluorescence and green fluorescence was scanned and observed, and the photograph was photographed and stored.

Figure 2:
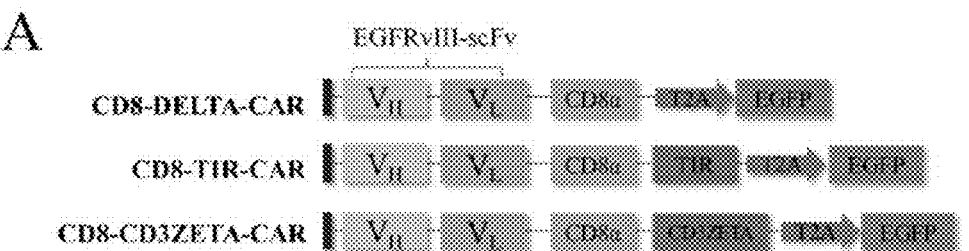
FIG. 2 shows construction of CAR-iMAC (chimeric antigen receptor-macrophage) and testing of non-specific basal phagocytic function thereof; A: constructing 3 CARs with different intracellular activation signal transduction domains and being capable of targeting GBM-specific membrane protein EGFRvIII; B: induced differentiation of iPSC (induced pluripotent stem cell) stably over-expressing CAR into CAR-iMAC; C: in vitro phagocytosis of U87MG (tdTomato) cell by CAR-iMAC (EGFP)
Figure 2:
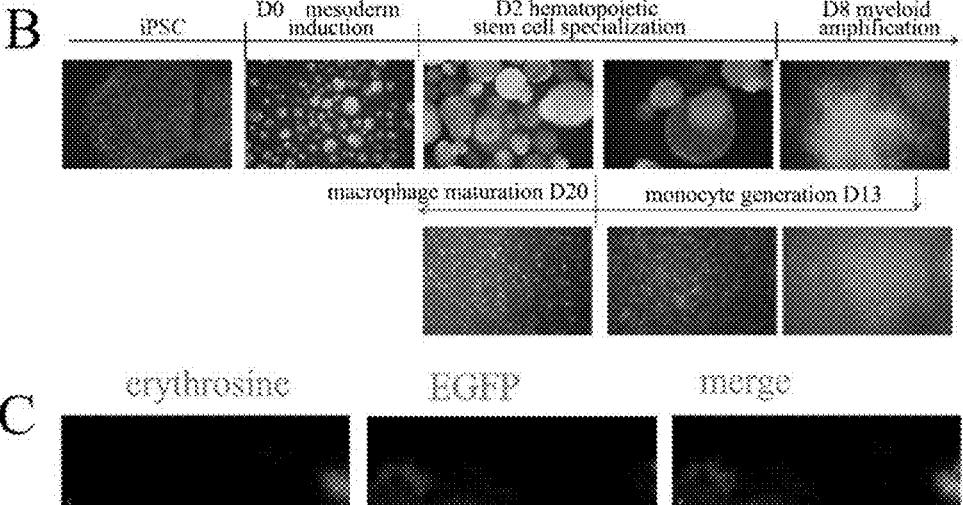

The construction of CAR-iMAC and the test of its non-specific basic phagocytosis function are as shown in FIG. 2, and the result shows that CAR-iMAC has the basic phagocytosis function.

Example 3

Assessing the ability of CAR-iMAC to kill GBM cell line in vitro.

The three different CAR-iMACs above and the control group cells iMAC were co-cultured in vitro with the U87MG$^{EGFRvIII}$ cells expressing luciferase in a living cell workstation according to effector-target ratios of 3:1, 5:1, and 10:1, respectively, to compare the effect of CAR containing different intracellular activation domains in enhancing the CAR-iMAC to target GBM and the effect of promoting its immune activation. The luciferase detecting experiment and the tumor cell flow counting experiment detected the targeted killing effects of different CAR-iMACs. The scFv-CD8-TIR-CAR was compared with the scFv-CD8-DELTA-CAR and scFv-CD8-CD3ZETA-CAR on the effects of CAR-iMAC polarization and activation according to the above indexes. Results are as shown in FIG. 3.

Figure 3:
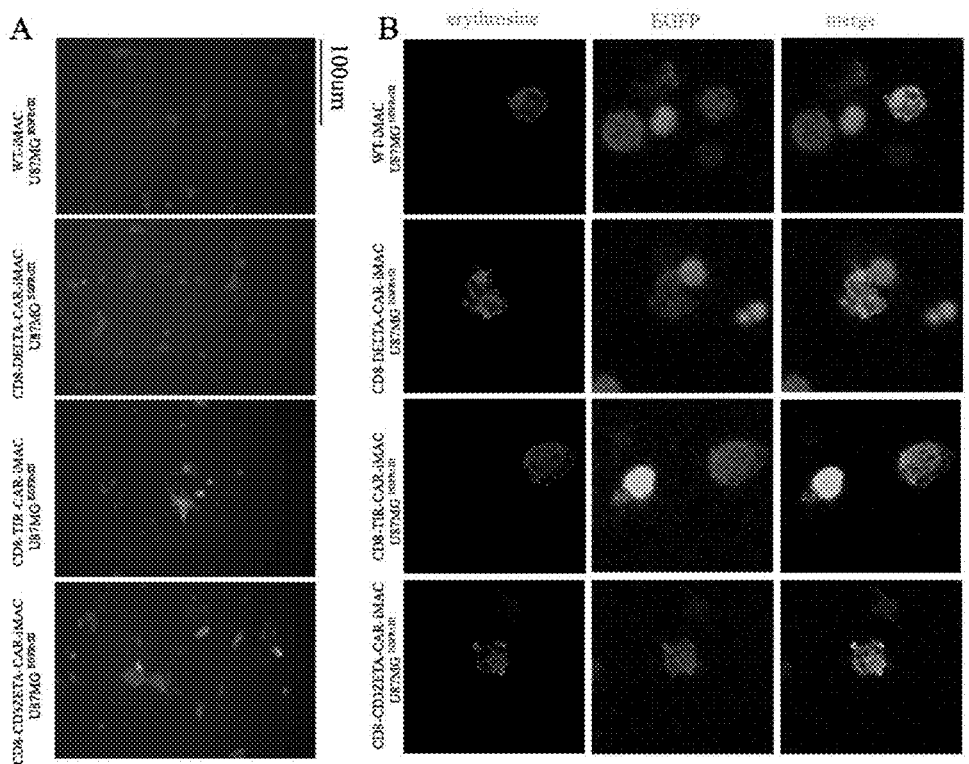
FIG. 3 shows CAR-iMAC targeting and killing U87MG$^{EGFRvIII}$ cell line in vitro; A: result after 12 hours of co-culturing in vitro; B: confocal scanning result.

In the above, the experimental steps in A in FIG. 3 are as follows:

1. Inoculating a certain number of 3 kinds of CAR-iMACs expressing green fluorescent protein and WT-iMAC (wild-type macrophage) into six-well plates, and polarizing the resultant in RPMI 1640 culture medium containing 100 ng/ml LPS (lipopolysaccharide), 100 ng/ml humanized INF-γ, 100 ng/ml M-CSF, and 100 ng/ml GM-CSF for 24 hours, in a 37° C./5% $CO_2$ cell incubator.
  2. Inoculating the 3 kinds of CAR-iMACs polarized obtained above, and WT-iMAC, respectively, with U87MG$^{EGFRvIII}$ cells expressing tdTomato red fluorescent protein at a 10:1 ratio into a glass bottom dish, co-culturing the resultant with RPMI1640 culture medium containing 100 ng/ml M-CSF and 100 ng/ml GM-CSF in a 37° C./5% $CO_2$ cell incubator for 12 hours.
  3. Placing the glass bottom dish in the previous step in an OLYPUS fluorescence microscope, and after setting the parameters, observing distribution situation of red fluorescence and green fluorescence, photographing and storing the photograph.

The experimental steps in B in FIG. 3 are as follows:
  1. Inoculating a certain number of 3 kinds of CAR-iMACs expressing green fluorescent protein and WT-iMAC into six-well plates, and polarizing the resultant in RPMI 1640 culture medium containing 100 ng/ml LPS, 100 ng/ml humanized INF-γ, 100 ng/ml M-CSF, and 100 ng/ml GM-CSF for 24 hours, in a 37° C./5% $CO_2$ cell incubator.
  2. Inoculating the polarized 3 kinds of CAR-iMACs obtained above, and WT-MAC, respectively, with U87MG$^{EGFRvIII}$ cells expressing tdTomato red fluorescent protein at a 10:1 ratio into a glass bottom dish, co-culturing the resultant with RPMI1640 culture medium containing 100 ng/ml M-CSF and 100 ng/ml GM-CSF in a 37° C./5% $CO_2$ cell incubator for 24 hours.

3. Placing the glass bottom dish in the previous step in a confocal fluorescence scanning microscope, and after setting the parameters, scanning and observing co-positioning situation of red fluorescence and green fluorescence, photographing and storing the photograph.

Figure 4:
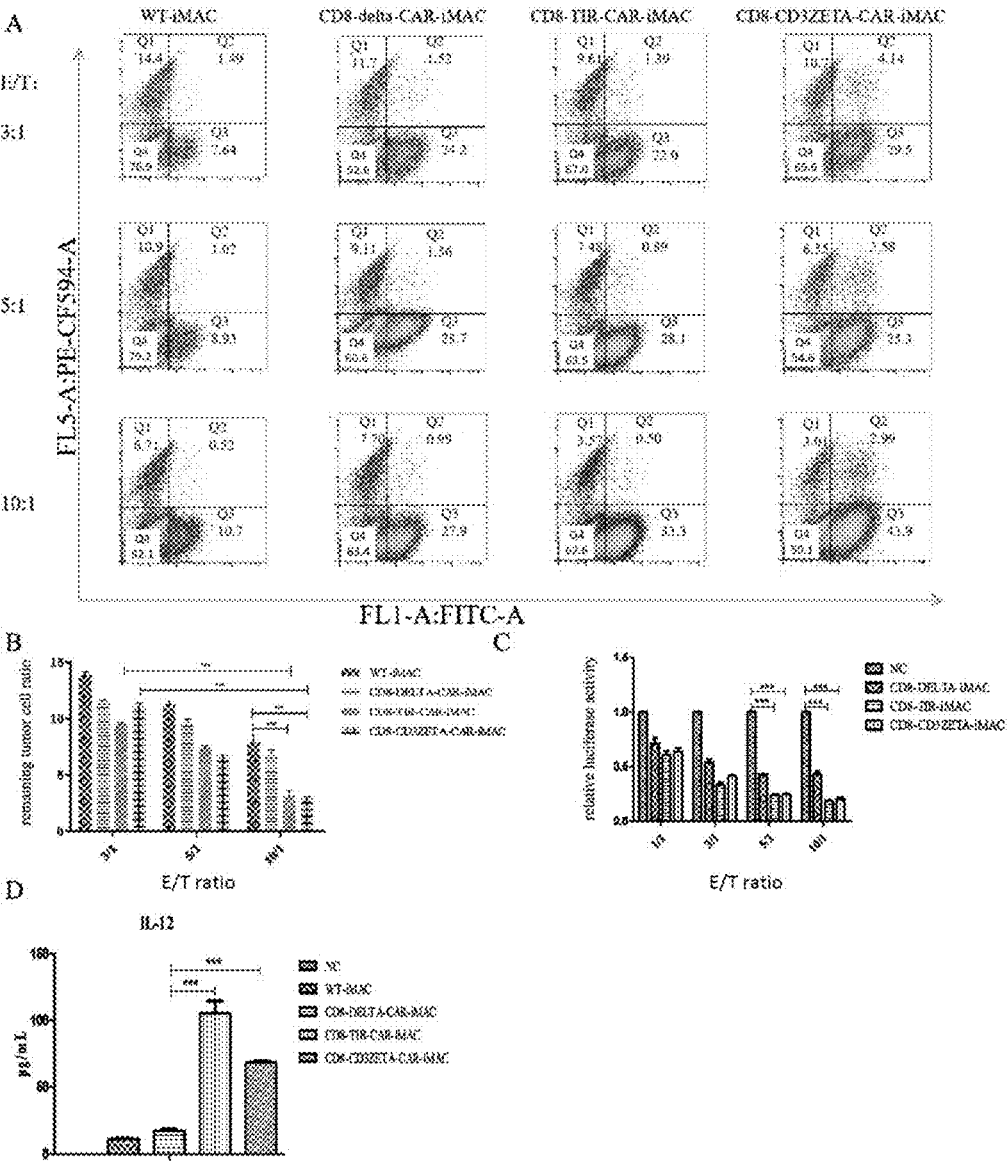
FIG. 4 shows results of flow analysis and ELISA experiment of CAR-iMAC in vitro targeting and killing U87MG$^{EGFRvIII}$ cell line; A: counting the number of tumor cells survived 24 hours after the co-culturing by the flow analysis technology; B: data statistical analysis of remaining tumor cell ratio in A; C: survival rate of tumor cells; D: detection of release situation of immune activating factors through ELISA assay.

Experimental steps of A and B in FIG. 4:

1. After polarizing the 3 kinds of CAR-iMACs expressing green fluorescent protein and WT-iMAC for 24 hours, co-culturing the resultant with U87MG$^{EGFRvIII}$ cells expressing tdTomato red fluorescent protein in six-well plates at ratios of 3:1, 5:1, and 10:1 for 24 hours (the method was the same as in B in FIG. 3).

2. Digesting the resultant by trypsin and collecting co-cultured cells, and detecting, counting, and analyzing the number of 3 kinds of CAR-iMACs, WT-iMAC, and U87MG$^{EGFRvIII}$ cells in a flow analyzer. The setting parameters are: the green fluorescent protein is an FITC channel, and the tdTomato is a PE channel.

Experimental steps in C in FIG. 4:

1. After polarizing the 3 kinds of CAR-iMACs expressing green fluorescent protein for 24 hours, co-culturing the resultant with U87MG$^{EGFRvIII}$ cells expressing luciferase of luciferase gene in 96-well plates in a light-tight condition at a ratio of 10:1 for 24 hours. Only the culture wells of U87MG$^{EGFRvIII}$ cells were set as negative control (NC) (the method was the same as in B in FIG. 3).

2. To a co-culture system adding 100 μl of luciferin at a concentration of 10 mg/ml to each well, and quickly placing the co-culture system in a multifunctional ELIASA to detect the fluorescence signal.

Experimental steps in D in FIG. 4:

1. Collecting a medium supernatant of the co-culture system in FIG. A, followed by 1000 rpm centrifugation for 20 minutes.

2. Adding 100 μl of the medium supernatant obtained in the previous step to corresponding detection wells of interleukin 12 (IL-12) enzyme-linked immunosorbent assay kit, detecting, by experiment via ELISA, the secretion situation of IL-12 after respectively co-culturing the 3 kinds of CAR-iMACs and WT-iMAC with U87MG$^{EGFRvIII}$ cells expressing tdTomato red fluorescent protein at a ratio of 10:1, and counting and analyzing the detected data.

The result shows that after three kinds of CAR-iMACs (EGFP) targeting EGFRvIII are co-cultured with U87MG$^{EGFRvIII}$ (tdTomato) for 12 hours in vitro, it is shown that different CAR-iMACs have stronger adhesion to U87MG$^{EGFRvIII}$ relative to WT-iMAC, meanwhile, U87MG$^{EGFRvIII}$ cell bodies were significantly larger than that of CAR-iMAC (A in FIG. 3). The confocal scanning shows that all of the three kinds of CAR-iMACs and WT-iMAC have the trogocytosis ability to U87MG$^{EGFRvIII}$ (B in FIG. 3).

After the three kinds of CAR-iMACs and WT-iMAC were co-cultured for 24 hours with U87MG$^{EGFRvIII}$ at the effector-target ratios of 3:1, 5:1, and 10:1, respectively, the number of tumor cells survived was counted by the flow analysis technology. The results show that both scFv-CD8-TIR-CAR-iMAC and scFv-CD8-CD3ZETA-CAR-iMAC have the ability to significantly kill U87MG$^{EGFRvIII}$, and the killing effect is more significant with increasing effector-target ratio (A and B in FIG. 4).

After the three kinds of CAR-iMACs were co-cultured in vitro with U87MG$^{EGFRvIII}$ cells stably expressing luciferase at different effector-target ratios for 24 hours, respectively, the survival rate of the tumor cells was characterized by detecting luciferase activity. The results are as shown in C in FIG. 4, indicating that scFv-CD8-TIR-CAR-iMAC and scFv-CD8-CD3ZETA-CAR-iMAC have significant ability to kill U87MG$^{EGFRvIII}$ cells relative to scFv-CD8-DELTA-CAR-iMAC at the effector-target ratios of 5/1 and 10/1.

After the three kinds of CAR-iMACs and WT-iMAC were co-cultured with U87MG$^{EGFRvIII}$ for 24 hours at an effector-target ratio of 10/1, respectively, the release situation of the immune activating factors was detected through the ELISA assay. The results are as shown in F in 3, indicating that scFv-CD8-TIR-CAR-iMAC and scFv-CD8-CD3ZETA-CAR-iMAC significantly up-regulate the secretion of the proinflammatory factor IL12 compared with WT-iMAC and scFv-CD8-DELTA-CAR-iMAC.

Example 4

Figure 5:
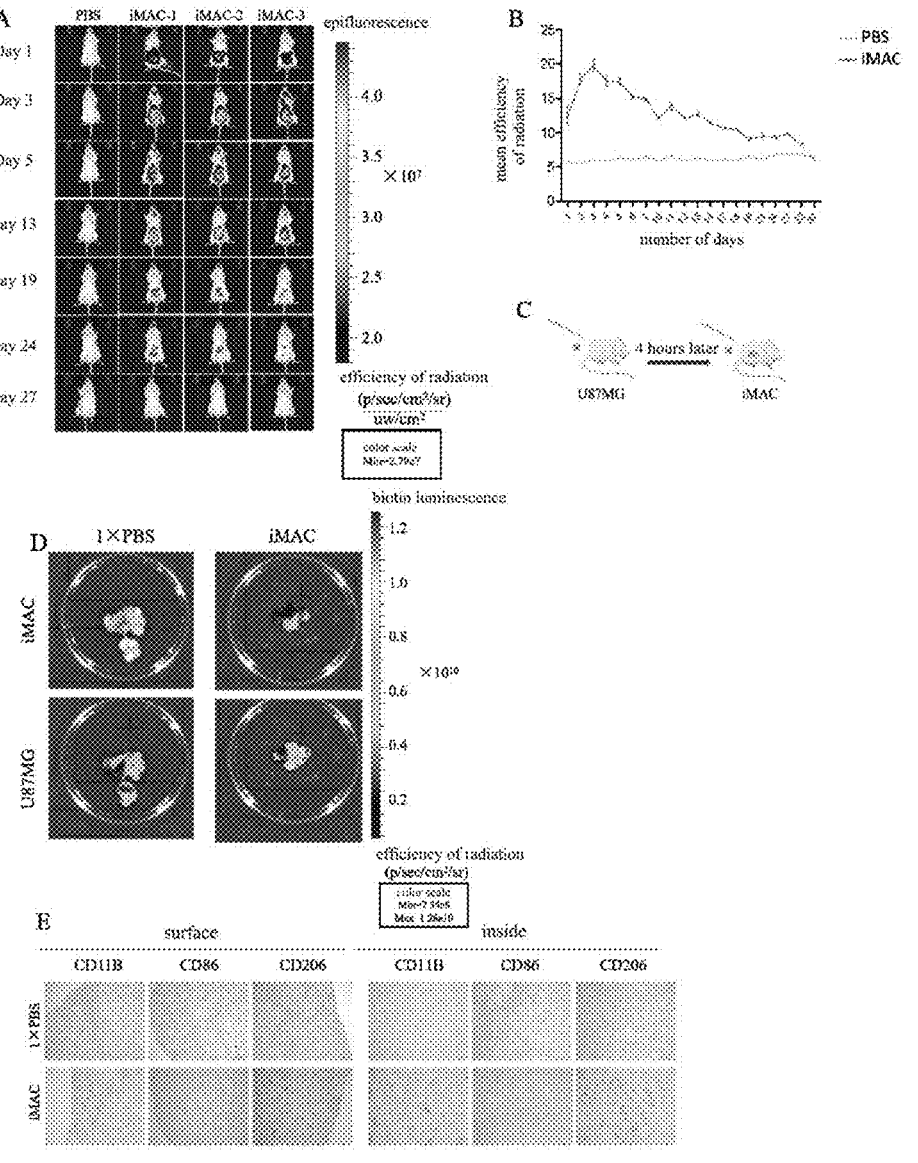
FIG. 5 shows tests of in vivo survival time of iMAC from iPSC and infiltration for solid tumor tissues; A: living body imaging detection of survival signal and time of iMAC; B: survival curve of iMAC in A through data statistics; C: experimental flowchart; D: infiltration situation of iMAC in tumor tissue; E: immunohistochemistry assay detection of infiltration situation of iMAC in tumor tissues.

Results of detections for survival time in vivo of the iMAC from the iPSC and infiltration thereof for physical tumor tissue are as shown in FIG. 5. NSG mice were intraperitoneally injected with fluorochrome Dir-labeled iMAC, and the survival signal and time of iMAC were detected by in vivo imaging, as shown in A in FIG. 5. Survival curve (B in FIG. 5) of iMAC in A in FIG. 5 by data statistics indicates that iMAC from iPSC may be present in the tumor model for more than 30 days, meeting the requirements of tumor immune cell therapy for the survival time required for immune cells.

$1×10^6$ U87MG cells over-expressing the Luciferase gene were intraperitoneally injected into the NSG mice, and 4 hours later, the same amount of iMACs were injected in situ. After 30 days, tumor tissues were isolated, and infiltration situation of iMACs in the tumor tissues was observed by Dir and Luciferin imaging, respectively. The results are as shown in D in FIG. 5, indicating the presence of iMAC in GBM. The infiltration situation of iMAC in tumor tissues was further detected through immunohistochemistry experiment, and the experimental steps are as follows:

1. Isolating tumor tissues after 30 days of intraperitoneal injection of iMAC into GBM mouse models, and fixing the tumor tissues in 4% PFA (paraformaldehyde) for one week.

2. Embedding the tissues: first adding some liquid paraffin to an iron mould, cooling the resultant slightly, then placing the tumor tissues fixed in the previous step in the paraffin, then covering a plastic mould cartridge, and finally, adding a little liquid paraffin for freezing, so that the paraffin turned into a solid state.

3. Slicing: removing the embedded tumor tissues from the mould, and placing the same on the paraffin slicer, wherein the slicer adjusted the tissues and cutting direction to be consistent by adjusting upper, lower, left, and right sides, then the thickness of the slice was adjusted, generally 5 μm, pulling the cut glass slide outwards with a hand, and placing the glass slide containing intact tissue in 40° C. warm water with pincettes.

4. Fishing out the tissues: removing bubbles in water bath, after the tissues were heated and unfolded, and fishing out 5-6 pieces of tissues in the same direction by lower ½ of the glass slide, then placing the glass slides taken out on a rack, to be dried in a 37° C. incubator.

5. Deparaffinating: placing the glass slide in xylene, xylene, 100% alcohol, 100% alcohol, 95% alcohol, 90% alcohol, 80% alcohol, and 70% alcohol in succession for deparaffinating, for 10-15 min in each reagent.

6. Antigen repair: after deparaffinating, rinsing the resultant in fresh water for a period of time, adding a citric acid buffer, steaming in a microwave oven for 3 min (medium heat) just to boil, cooling at room temperature, then steaming once again, and cooling to room temperature to expose the site of the antigen.

7. Sealing with serum: after cooling to room temperature, pouring off the citric acid buffer, washing twice with water, placing the glass slide in the PBS for 5 min, washing twice, and wiping dry the PBS liquid around the tissues, immediately adding serum diluted ten times with PBS, to seal some non-specific sites, and then placing the glass slide in a 37° C. incubator for half an hour.

8. Adding a primary antibody: taking out the glass slide from the incubator, wiping dry the serum around the back side and tissues at front side of the glass slide with absorbent paper, and dropping the primary antibodies of CD11b, CD86, and CD206, respectively, storing overnight in a 4° C. refrigerator.

9. Adding a secondary antibody: taking the glass slide from the refrigerator, placing the glass slide in the PBS for washing for 3 times, 5 min each time, adding a secondary antibody of the same species after wiping dry the PBS around the tissues, and then placing the glass slide in a 37° C. incubator for half an hour.

10. Adding SABC: taking the glass slide from the incubator, placing the glass slide in the PBS for washing for 3 times, 5 min each time, adding SABC diluted 100 times with PBS after wiping dry the PBS around the tissues, and then placing the glass slide in a 37° C. incubator for half an hour.

11. Adding a color developing agent: taking the glass slide from the incubator, placing the glass slide in the PBS for washing for 3 times, 5 min each time, adding the color developing agent after wiping dry the PBS around the tissues (configuration of the color developing agent: adding 1 drop of color developing agent A to 1 ml of water, shaking well the resultant, then adding 1 drop of color developing agent B, shaking well the resultant, then adding 1 drop of color developing agent C, and shaking well the resultant. A: DAB, B: H202, C: phosphoric acid buffer.

12. Re-staining: after rinsing the developed glass slide with fresh water for a period of time, soaking the glass slide in hematoxylin for staining, generally half minutes for animal tissues, and 3-5 min for plant tissues.

13. Dehydration: after rinsing the re-stained glass slide in water, placing the glass slide in 70% alcohol, 80% alcohol, 90% alcohol, 95% alcohol, 100% alcohol, xylene, and xylene in succession, for 2 min in each reagent, finally soaking the glass slide in xylene, and transferring the glass slide into a fume hood.

14. Sealing the glass slide: dropping neutral gum beside the tissues, and then covering the glass slide lightly with a coverslip (wherein one side should be laid flat first, then the other side was laid down gently, so as to avoid generation of air bubbles), and then placing the sealed glass slide in the fume hood for drying.

15. Imaging: placing the tumor histochemistry samples obtained above in an OLYMPUS upright microscope, and setting up the same for imaging and taking pictures.

The results are as shown in E in FIG. 5, indicating that iMAC has the ability to infiltrate to the inside of solid tumors and exists in the form of M2 type macrophage.

Example 5

Constructing GBM Mouse Abdominal Tumor Models $2 \times 10^6$ U87MG$^{EGFRvIII}$ cells over-expressing the luciferase gene were inoculated into the abdominal cavity of NSG mice in a manner of abdominal injection, respectively, to construct the abdominal GBM mouse models.

Validation of CAR-iMAC Anti-Tumor Capacity In Vivo in GBM Models

The above three different kinds of CAR-iMACs and their control cells iMACs were adoptively transplanted into the abdominal GBM mouse models. Changes in tumor, change situation of mouse body weight and survival state were observed and recorded as appropriate by mouse in vivo imaging technology. Results are as shown in FIG. 6.

Figure 6:
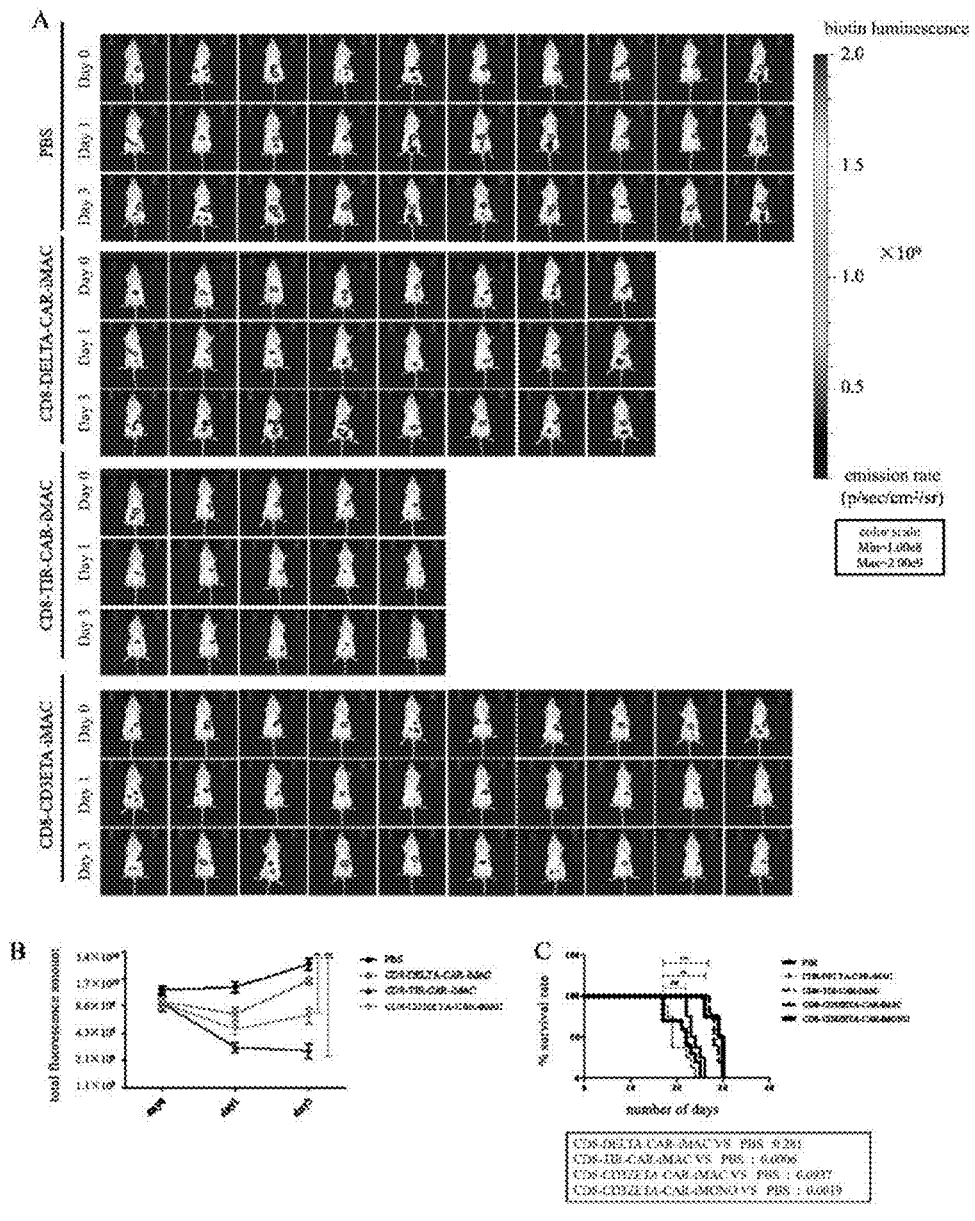
FIG. 6 shows tumor killing effects of CAR-iMAC verified in GBM mouse tumor models; A: respective killing effects of three kinds of CAR-iMACs on GBM (Luciferin biotin luminescence); B: change situation of tumor signal; C: survival time of GBM mice treated by different CAR-iMACs.

After injection of three kinds of CAR-iMACs (scFv-CD8-DELTA-CAR-iMAC, scFv-CD8-TIR-CAR-iMAC, scFv-CD8-CD3ZETA-CAR-iMAC) (DiR) and PBS, respectively, in the NSG mouse GBM abdominal cavity models, the killing effects of the three kinds of CAR-iMACs on GBM (Luciferin biotin luminescence) at the effector-target ratio of 10/1 was displayed through the in vivo imaging technology, as shown in A in FIG. 6, and change situation of tumor signal of GBM in the presence of three kinds of CAR-iMACs and the survival time of GBM mice after treatment (B and C in FIG. 6), respectively. The results indicate that scFv-CD8-TIR-CAR-iMAC has a stronger in vivo anti-tumor function relative to scFv-CD8-CD3ZETA-CAR-iMAC.

Example 6

Figure 7:
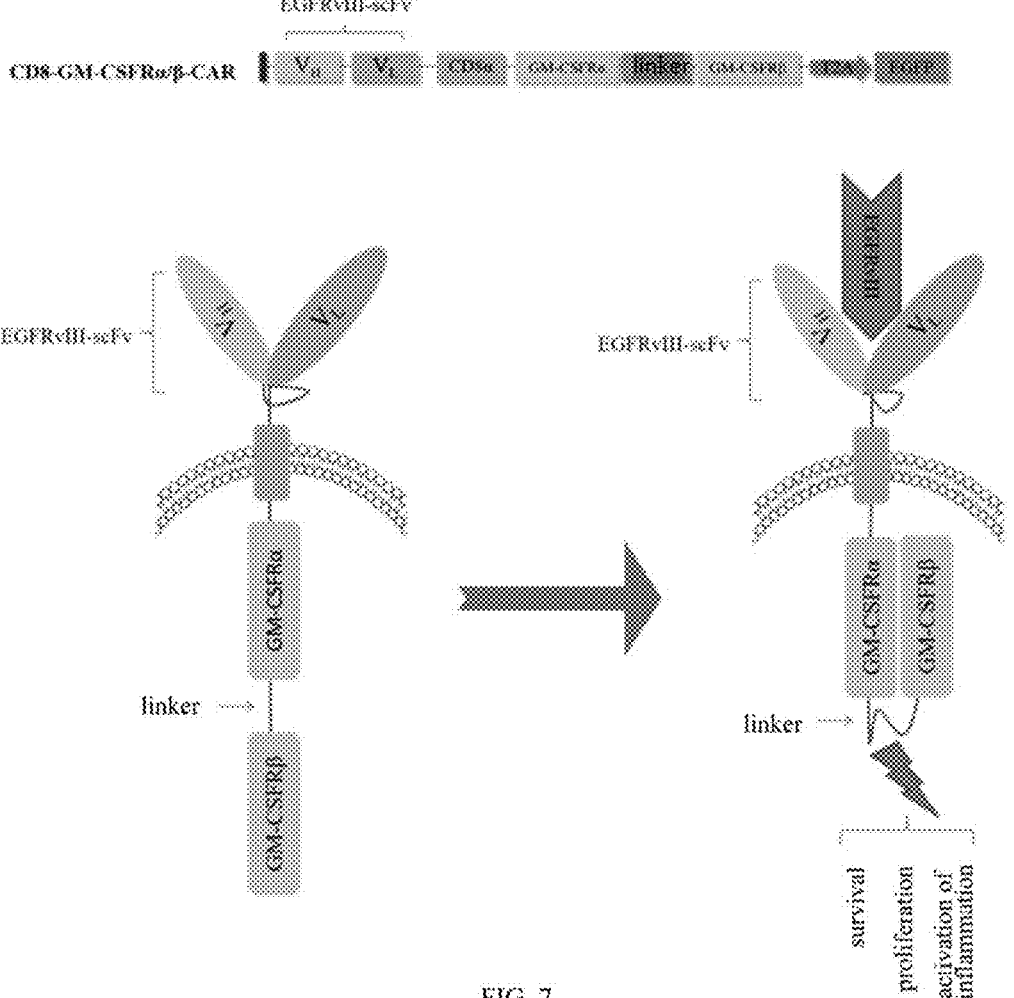
FIG. 7 shows a structural diagram of CD8-GM-CSFRα/β-CAR and a schematic diagram of activation thereof.

A chimeric antigen receptor CD8-GM-CSFRα/β-CAR, of which a structural schematic diagram and an activation schematic diagram thereof are as shown in FIG. 7. A in FIG. 7 shows that CD8-GM-CSFRα/β-CAR is composed of a scFv protein sequence extracellularly recognizing EGFRvIII, a CD8α transmembrane domain, and an intracellular signal transduction domain. The intracellular signal transduction domain consists of an intracellular signal activation domain of receptor GM-CSFRα and an intracellular signal activation domain of receptor GM-CSFRβ that are linked by a Linker sequence. The linker sequence may flexibly change the conformation thereof. B in FIG. 7 shows that after the extracellular scFv of the CD8-GM-CSFRα/β-CAR contacts the EGFRvIII protein to form an immunological synapse, the intracellular GM-CSFRα and GM-CSFRβ activation domains form heterodimer by changing the linker conformation, and then are activated, which finally promotes the proliferation, immune activation, and phagocytosis of the CAR-iMAC.

Example 7

In vitro verification of effects of CD8-GM-CSFRα/β-CAR-iMAC targeted killing and immune activation thereof depending on CAR.

Figure 8:
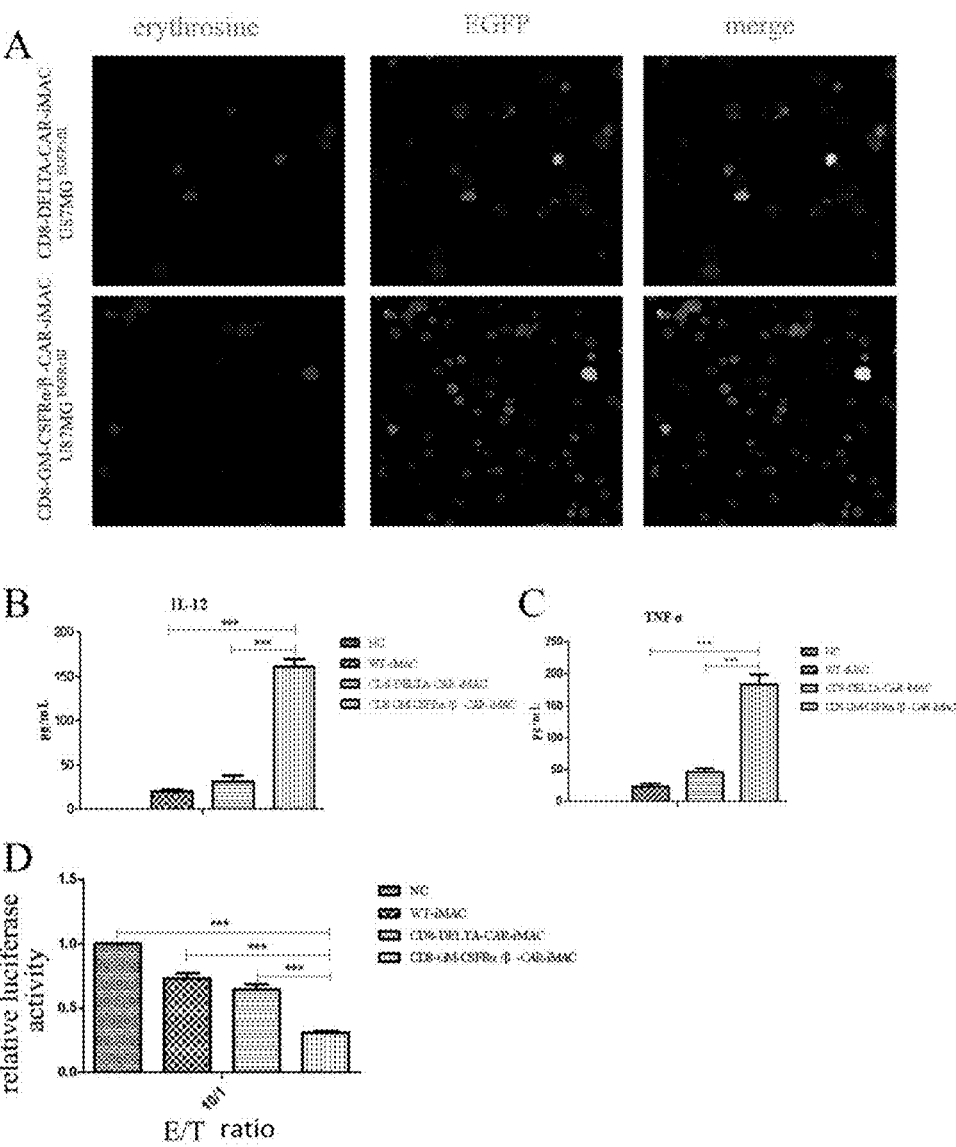
FIG. 8 shows in vitro verification of CD8-GM-CSFRα/β-CAR-iMAC targeted killing and effects of immune activation depending on CAR.

According to the experimental method of B in FIG. 3 in Example 3, CD8-GM-CSFRα/β-CAR-iMAC and CD8-DELTA-CAR-iMAC were co-cultured in vitro in a living cell workstation for 24 h with U87MG$^{EGFRvIII}$ cells expressing luciferase, and after co-culturing for 24 h in vitro, CD8-GM-CSFRα/β-CAR-iMAC (EGFP) and CD8-DELTA-CAR-iMAC (EGFP) without an intracellular signal transduction domain both had the ability to phagocytose U87MG$^{EGFRvIII}$ cells as shown by confocal scanning (A in FIG. 8). WT-iMAC, CD8-DELTA-CAR-iMAC, and CD8-GM-CSFRα/β-CAR-iMAC were respectively co-cultured with U87MG$^{EGFRvIII}$ cells in vitro for 24 h at an effector-target ratio of 10/1, and then the secretion situation of macrophage immune activating factors IL-12 and TNFα were detected by ELISA assay. The results are as shown in B and C in FIG. 8, indicating that CD8-GM-CSFRα/β-CAR-iMAC has significant ability to secrete IL-12 and TNFα relative to WT-iMAC and CD8-DELTA-CAR-iMAC. WT-iMAC, CD8-DELTA-CAR-iMAC, and CD8-GM-CSFRα/β-CAR-iMAC were respectively co-cultured in vitro with U87MG$^{EGFRvIII}$ cells expressing the luciferase for 24 h at an effector-target ratio of 10/1, and then the fluorescence signal in U87MG$^{EGFRvIII}$ cells were detected by a multifunctional ELIASA. The results are as shown in D in FIG. 8, indicating that the fluorescence signal is significantly down-regulated after co-culturing of U87MG$^{EGFRvIII}$ cells and CD8-GM-CSFRα/β-CAR-iMAC. It is further verified that CD8-GM-CSFRα/β-CAR-iMAC has more significant ability to kill U87MG$^{EGFRvIII}$ cells relative to WT-iMAC and CD8-DELTA-CAR-iMAC.

Finally, it should be explained that the various examples above are merely used for illustrating the technical solutions of the present disclosure, rather than limiting the present disclosure, although the detailed description is made to the present disclosure with reference to various preceding examples, those ordinarily skilled in the art should understand that they still could modify the technical solutions recited in various preceding examples, or make equivalent substitutions to some or all of the technical features therein, and these modifications or substitutions do not make the corresponding technical solutions essentially depart from the scope of the technical solutions of various examples of the present disclosure.

INDUSTRIAL APPLICABILITY

The chimeric antigen receptor provided in the present disclosure can endow the macrophage with the property of targeting GBM, reduce off-target effect, promote and maintain the M1 polarization state of the macrophage in a tumor microenvironment, and improve killing efficiency of the macrophage. The polarization method of macrophage provided in the present disclosure is simple, and can realize M1 polarization of the macrophage. The macrophage provided in the present disclosure can maintain the M1 polarization state, and has strong targeted killing property to GBM. The macrophage can stably over-express the chimeric antigen receptor for a long time, and can solve the problems such as low editing efficiency, long cycle, heavy workload, and delayed treatment in current immune cell therapy. The pluripotent stem cell provided in the present disclosure contains the gene encoding the above chimeric antigen receptor, the state of the pluripotent stem cell is more prone to the M1 state pro-inflammatory and suppressing tumor, and the pluripotent stem cell can be optionally differentiated to obtain the macrophage, which is more favorable for suppressing the tumor, and has a wider application prospect and higher market value.

What is claimed is:

1. A chimeric antigen receptor, comprising an extracellular antigen binding domain, a transmembrane domain, and an intracellular activation domain that are linked in sequence, wherein the extracellular antigen binding domain comprises a signal peptide and/or a scFv targeting EGFRvIII;

the transmembrane domain comprises CD8α; and the intracellular activation domain comprises GM-CSFRα/β;

optionally, the intracellular activation domain further comprises at least one of TIR or CD3ZETA, wherein the GM-CSFRα/β is expressed by a nucleotide sequence represented by SEQ ID NO.6.

2. The chimeric antigen receptor according to claim 1, wherein the signal peptide is expressed by a nucleotide sequence represented by SEQ ID NO.1; and the scFv is expressed by a nucleotide sequence represented by SEQ ID NO.2.

3. The chimeric antigen receptor according to claim 1, wherein the TIR comprises an intracellular signal transduction domain derived from TLR1, TLR2, TLR3, TLR4, TLR5, TLR6, TLR7, TLR8, TLR9, TLR10, TLR13 or TLR19, wherein the intracellular signal transduction domain of the TLR4 is expressed by a nucleotide sequence represented by SEQ ID NO.4;

the CD3ZETA is expressed by a nucleotide sequence represented by SEQ ID NO.5.

4. A polarization method of macrophage, comprising making the chimeric antigen receptor according to claim 1 expressed in the macrophage.

5. A macrophage, comprising the chimeric antigen receptor according to claim 1.

6. The chimeric antigen receptor according to claim 2, wherein the CD8α is expressed by a nucleotide sequence represented by SEQ ID NO.3.

7. The chimeric antigen receptor according to claim 2, wherein the TIR comprises an intracellular signal transduc-5 tion domain derived from TLR1, TLR2, TLR3, TLR4, TLR5, TLR6, TLR7, TLR8, TLR9, TLR10, TLR13 or TLR19, wherein the intracellular signal transduction domain of the TLR4 is expressed by a nucleotide sequence represented by 10 SEQ ID NO.4;

the CD3ZETA is expressed by a nucleotide sequence represented by SEQ ID NO.5.

\* \* \* \* \*